(12) United States Patent
Wang et al.

(10) Patent No.: US 8,873,712 B2
(45) Date of Patent: *Oct. 28, 2014

(54) EXPOSURE CONTROL USING DIGITAL RADIOGRAPHY DETECTOR

(75) Inventors: Xiaohui Wang, Pittsford, NY (US);
David H. Foos, Webster, NY (US);
Michael C. Lalena, Webster, NY (US)

(73) Assignee: Carestream Health, Inc., Rochester, NY (US)

( * ) Notice: Subject to any disclaimer, the term of this patent is extended or adjusted under 35 U.S.C. 154(b) by 127 days.

This patent is subject to a terminal disclaimer.

(21) Appl. No.: 13/083,765

(22) Filed: Apr. 11, 2011

(65) Prior Publication Data

US 2011/0249791 A1 Oct. 13, 2011

Related U.S. Application Data

(60) Provisional application No. 61/323,476, filed on Apr. 13, 2010, provisional application No. 61/449,932, filed on Mar. 7, 2011.

(51) Int. Cl.
*H05G 1/64* (2006.01)
*A61B 6/00* (2006.01)
*A61B 6/08* (2006.01)

(52) U.S. Cl.
CPC . *A61B 6/08* (2013.01); *A61B 6/461* (2013.01); *A61B 6/4208* (2013.01); *A61B 6/587* (2013.01); *A61B 6/542* (2013.01); *A61B 6/4405* (2013.01); *A61B 6/547* (2013.01); *A61B 6/4266* (2013.01)
USPC ............................................. 378/97; 378/108

(58) Field of Classification Search
USPC .................................. 378/98.18, 97, 95, 108
See application file for complete search history.

(56) References Cited

U.S. PATENT DOCUMENTS

| | | | |
|---|---|---|---|
| 4,017,858 A | | 4/1977 | Kuipers |
| 4,246,486 A | | 1/1981 | Madsen |
| 4,752,948 A | | 6/1988 | MacMahon |
| 4,836,671 A | | 6/1989 | Bautista |
| 5,241,578 A | | 8/1993 | MacMahon |
| 5,388,143 A | | 2/1995 | MacMahon |
| 5,539,798 A | * | 7/1996 | Asahina et al. ............. 378/98.5 |
| 5,550,889 A | | 8/1996 | Gard et al. |

(Continued)

FOREIGN PATENT DOCUMENTS

JP 2000-023955 1/2000

OTHER PUBLICATIONS

One-page brochure for EasyPos dental x-ray positioning system from website, Mar. 2010. hyphendev.fr file PubEasypos08v3.pdf.

(Continued)

*Primary Examiner* — Hoon Song

(57) ABSTRACT

A method for sensing a level of ionizing radiation directed from a radiation source through a subject and toward a digital radiography detector, executed at least in part by a logic processor, obtains image data that relates the position of the subject to the digital radiography detector and assigns one or more radiant-energy sensing elements of the digital radiography detector as one or more exposure control sensing elements. The one or more exposure control sensing elements are sampled one or more times during exposure to measure the exposure directed to the subject. A signal is provided to terminate exposure according to exposure measurements obtained from the one or more exposure control sensing elements within the digital radiography detector.

19 Claims, 26 Drawing Sheets

(56) References Cited

U.S. PATENT DOCUMENTS

| | | | |
|---|---|---|---|
| 5,617,462 | A | 4/1997 | Spratt |
| 5,751,783 | A | 5/1998 | Granfors et al. |
| 5,949,811 | A | 9/1999 | Baba et al. |
| 6,047,042 | A | 4/2000 | Khutoryansky et al. |
| 6,154,522 | A | 11/2000 | Cumings |
| 6,192,105 | B1 | 2/2001 | Hunter et al. |
| 6,208,710 | B1 | 3/2001 | Nagai |
| 6,327,336 | B1 | 12/2001 | Gingold et al. |
| 6,404,851 | B1 | 6/2002 | Possin et al. |
| 6,422,750 | B1 | 7/2002 | Kwasnick et al. |
| 6,702,459 | B2 | 3/2004 | Barnes et al. |
| 6,760,405 | B2 | 7/2004 | Ruetten et al. |
| 6,895,268 | B1 | 5/2005 | Rahn et al. |
| 6,942,385 | B2 | 9/2005 | Fadler et al. |
| 6,944,266 | B2 | 9/2005 | Yamazaki et al. |
| 6,950,492 | B2 | 9/2005 | Besson |
| 7,010,091 | B2 | 3/2006 | Hayashida et al. |
| 7,120,229 | B2 | 10/2006 | Takasawa |
| 7,156,553 | B2 | 1/2007 | Tanaka et al. |
| 7,345,274 | B2 | 3/2008 | Nilsson |
| 7,368,724 | B2 | 5/2008 | Morii et al. |
| 7,490,986 | B2 | 2/2009 | Takekoshi et al. |
| 7,519,155 | B2 | 4/2009 | Mollus et al. |
| 7,581,884 | B1 | 9/2009 | Barnes et al. |
| 7,601,961 | B2 | 10/2009 | Franklin et al. |
| 7,613,276 | B2 | 11/2009 | Sendai |
| 7,632,016 | B1 | 12/2009 | Huang et al. |
| 7,744,279 | B2 | 6/2010 | Heath et al. |
| 7,780,350 | B2 | 8/2010 | Tranchant et al. |
| 7,794,144 | B2 | 9/2010 | Windt |
| 7,798,710 | B1 | 9/2010 | Barnes et al. |
| 2002/0150215 | A1 | 10/2002 | Barnes et al. |
| 2002/0188194 | A1 | 12/2002 | Cosman |
| 2003/0165216 | A1 | 9/2003 | Walker et al. |
| 2004/0101100 | A1* | 5/2004 | Morii et al. .................. 378/98.7 |
| 2004/0105526 | A1 | 6/2004 | Zhang et al. |
| 2005/0058244 | A1 | 3/2005 | Tanaka et al. |
| 2005/0169425 | A1 | 8/2005 | Takasawa |
| 2006/0109958 | A1 | 5/2006 | Ertel et al. |
| 2006/0269114 | A1 | 11/2006 | Metz |
| 2007/0030957 | A1 | 2/2007 | Pommi |
| 2007/0244388 | A1 | 10/2007 | Sato et al. |
| 2007/0255087 | A1 | 11/2007 | Minai |
| 2007/0297569 | A1 | 12/2007 | Saunders |
| 2008/0130837 | A1 | 6/2008 | Heath et al. |
| 2008/0198968 | A1 | 8/2008 | Takekoshi et al. |
| 2008/0204012 | A1 | 8/2008 | Krueger et al. |
| 2008/0240346 | A1 | 10/2008 | Kashiwagi et al. |
| 2009/0060145 | A1 | 3/2009 | Tranchant et al. |
| 2009/0086926 | A1 | 4/2009 | Wang et al. |
| 2009/0136000 | A1 | 5/2009 | Nishii et al. |
| 2009/0180590 | A1 | 7/2009 | Borgmann et al. |
| 2009/0257561 | A1 | 10/2009 | Okuno et al. |
| 2010/0002831 | A1 | 1/2010 | Maack |

OTHER PUBLICATIONS

International Search Report & Written Opinion, International application No. PCT/US2011/032020, date Nov. 22, 2011, 8 pages.

International Search Report & Written Opinion, International application No. PCT/US2011/032035, dated Dec. 19, 2011, 9 pages.

International Search Report, International application No. PCT/US2012/0262212, dated Aug. 30, 2012, 2 pages.

Supplementary European Search Report completed Mar. 5, 2014 for European Patent Application No. 11 76 9395.2, 2 pages.

Supplementary Partial European Search Report completed Apr. 29, 2014 for European Patent Application No. 11 76 9406, 1 page.

* cited by examiner

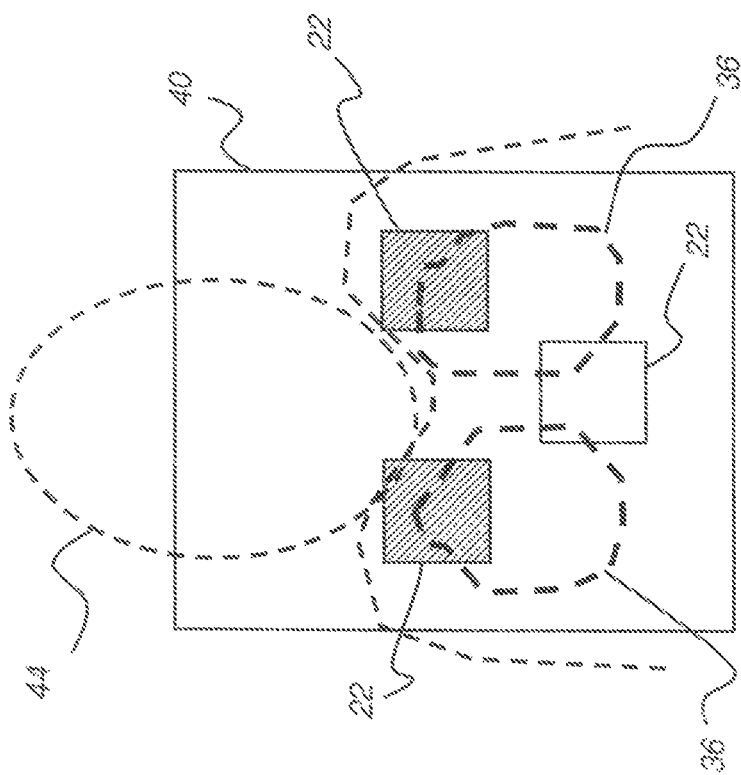

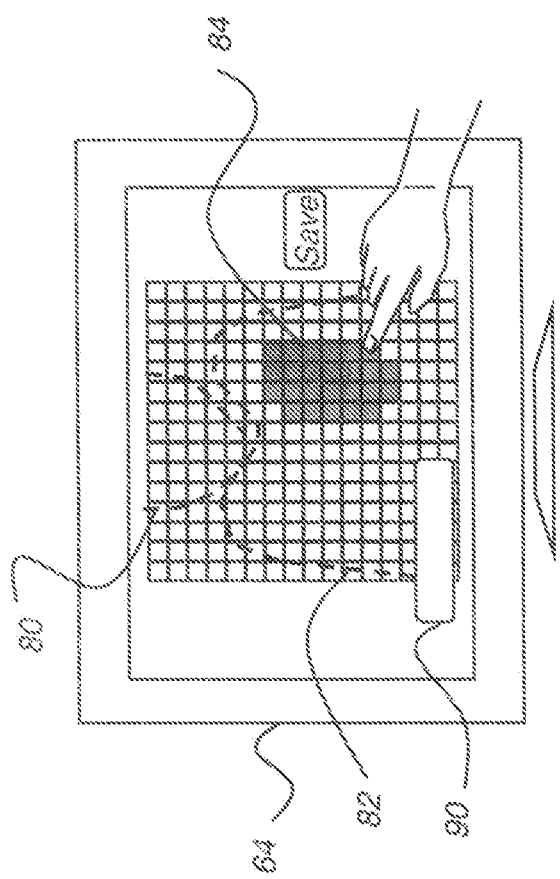

EXPOSURE CONTROL USING DIGITAL RADIOGRAPHY DETECTOR

CROSS REFERENCE TO RELATED APPLICATION

This application claims priority to Provisional Application Ser. No. 61/323,476, filed 13 Apr. 2010, entitled "MOBILE UNIT HAVING TUBE ALIGNMENT SYSTEM," by Lalena, incorporated herein by reference.

This application claims priority to Provisional Application Ser. No. 61/449,932, filed 7 Mar. 2011, entitled "GRAPHIC USER INTERFACE FOR MOBILE UNIT," by Stagnitto, incorporated herein by reference.

This application relates to U.S. patent application Ser. No. 13/083,780 entitled "CONFIGURABLE AEC SENSOR FOR AN X-RAY SYSTEM" in the name of Lalena, filed on even date, now U.S. Pat. No. 8,824,634.

This application relates to U.S. patent application Ser. No. 13/083,776 entitled "DISPLAY OF AEC SENSOR LOCATION" in the name of Wang, filed on even date.

FIELD OF THE INVENTION

The invention relates generally to the field of radiographic imaging and more particularly relates to apparatus and methods for control of exposure energy in an X-ray system.

BACKGROUND OF THE INVENTION

Automatic Exposure Control (AEC) apparatus are widely used in conventional diagnostic X-ray equipment to control X-ray exposure levels received by a patient. Using an AEC device can help to limit the amount of radiation that is received by sensing the radiation level at a suitable location in the exposure path and providing an output signal that indicates when sufficient radiation has been received. This output signal is then used to disable power to the X-ray emission components, thereby stopping the generation of ionizing radiation.

The schematic block diagram of FIG. 1A shows an X-ray imaging system 10 that is used to provide a radiographic image of a patient or other subject 14. When the technician operates a control 24, an X-ray source 16 generates the ionizing radiation that is used for exposure and for forming an image onto a detector 12. An Automatic Exposure Control (AEC) apparatus 20 has one or more sensor elements 22 that respond to incident radiation by generating a signal that indicates the amount of radiation received. A generator control 18 interprets this signal and responds to terminate x-ray emission at an appropriate point.

AEC sensor elements 22 are typically located at suitable locations just behind the patient or other subject 14 in order to sense the amount of radiation received over particular areas of subject 14. Sensor elements 22 may be individual sensor elements, or may be integrated into a panel that is positioned behind the patient, as suggested in FIG. 1A. In other embodiments, sensor elements 22 of the AEC apparatus 20 are provided on the surface of detector 12 or in the bucky or other holder that is used for retaining detector 12.

The basic schematic diagram of FIG. 1A can be used with any type of X-ray detector technology, that is, with film, with computed radiography (CR) plates, or with a digital radiography (DR) flat panel detector.

The plan view of FIG. 1B shows a conventional arrangement of AEC apparatus 20 having three sensor elements 22. In conventional use, AEC sensor elements 22 are in fixed positions in front of the X-ray detector 12; in some systems, detector 12 or a plate holding AEC sensor elements 22 can be rotated within the plane in order to position the sensor element 22 devices appropriately with respect to the patient. Signals from individual sensor elements 22 are collected and combined for transmission to generator control circuitry.

The use of a standard pattern of AEC sensor elements 22 in fixed positions, as shown in FIG. 1B can present some problems. AEC sensor elements 22 work best when placed behind the area of bone or tissue that is of most diagnostic interest. This area can differ from one patient to the next. In addition, patient body size and proportions vary over a range, so that no one fixed pattern of AEC sensor elements 22 works optimally for all patient sizes and for all imaging situations. Some compromise is made for imaging under particular conditions when using the conventional AEC arrangement.

In some conventional x-ray systems, one or more AEC sensor elements 22 can be disabled for a particular image, allowing the operator to compensate somewhat for differences in the anatomy being imaged or for patient positioning. However, this solution can mean less accurate detection of the exposure level and risks over- or under-exposure for obtaining the image of the patient or other subject.

There are a number of inherent problems with using conventional AEC apparatus. One problem relates to obstruction of a portion of the image signal. As shown in the example of FIG. 1A, the AEC sensor elements 22 are disposed in the imaging path, prior to detector 12. Even though AEC sensor elements 22 are fabricated of low-density materials that reduce their interference with signal content, some amount of signal degradation occurs due to the AEC device. Another problem relates to fixed positioning; AEC sensor elements 22 are not always in the best position for obtaining an image due to differences in types of anatomy imaged, patient size, and, particularly with portable radiography apparatus, variable detector 12 positioning relative to subject 14 and to the AEC sensor elements 22.

Thus, it can be seen that a more flexible arrangement for AEC sensing would have advantages for adapting to different patients and to different imaging applications.

SUMMARY OF THE INVENTION

An object of the present invention is to address the need for greater flexibility in the use of exposure control sensors in diagnostic imaging applications. Advantageously, methods and apparatus of the present invention provide an arrangement of exposure sensor elements that allows their individual addressing, enablement, and grouping, thereby allowing configuration of sensors to suit the conditions of each particular x-ray exam.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the present invention there is provided a method for sensing a level of ionizing radiation directed from a radiation source through a subject and toward a digital radiography detector, the method executed at least in part by a logic processor and comprising: obtaining image data that relates the position of the subject to the digital radiography detector; assigning one or more radiant-energy sensing elements of the digital radiography detector as one or more exposure control sensing elements, according to the obtained image data; sampling the one or more exposure control sensing elements one or more times during exposure to measure the exposure directed to the subject; and providing a signal to terminate exposure according to exposure measurements obtained from the one or more exposure control sensing elements within the digital radiography detector.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 2F is a plan view of an AEC apparatus with a conventional arrangement of non-composite radiation measurement regions, also usable in embodiments of the present invention.

FIG. 5B is a plan view of a display showing technician configuration of an AEC apparatus using a traced pattern on a touchscreen.

DETAILED DESCRIPTION OF THE INVENTION

Figure 1A:
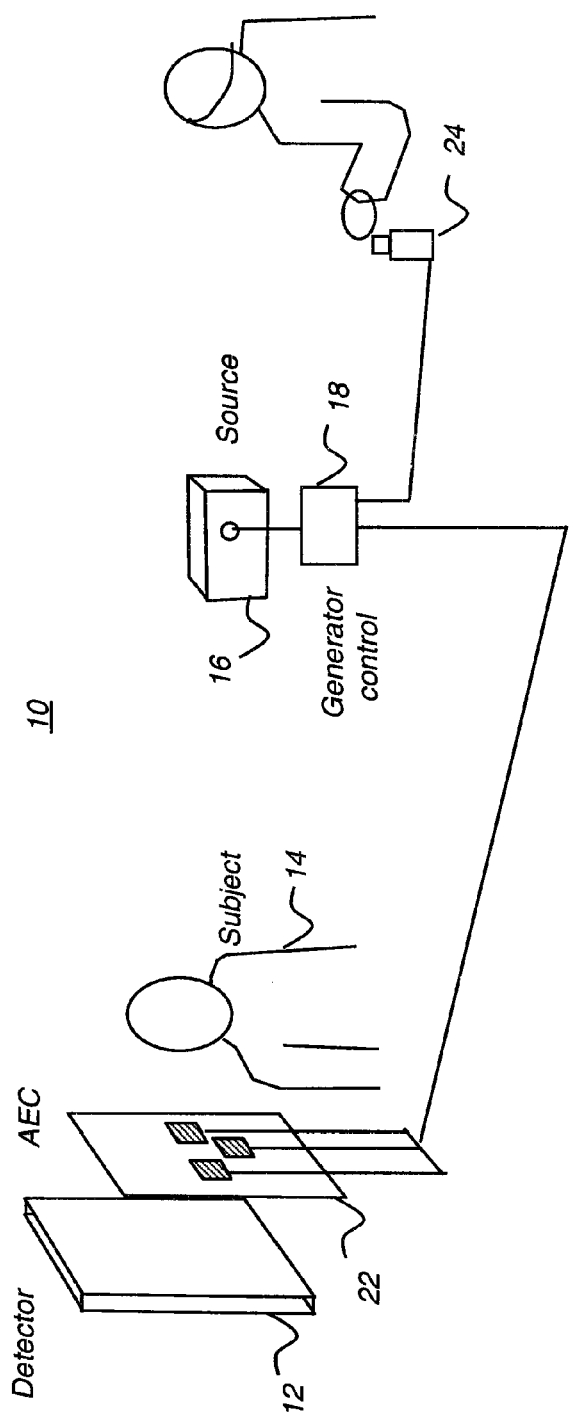
FIG. 1A is a block diagram showing components of a conventional radiographic imaging apparatus.

The following is a detailed description of the preferred embodiments of the invention, reference being made to the drawings in which the same reference numerals identify the same elements of structure in each of the several figures.

In the context of the present disclosure, the use of terms such as "first", "second", "third", etc., does not by itself connote any priority, precedence, or order of a component or claim element over another or the temporal order in which acts of a method are performed. These terms may be used more generally as labels to distinguish one element having a certain name from another element having the same name (but for use of the ordinal term) or to distinguish the claim elements.

The term "set", as used herein, refers to a non-empty set, as the concept of a collection of elements or members of a set is widely understood in elementary mathematics. The term "subset", unless otherwise explicitly stated, is used herein to refer to a non-empty proper subset, that is, to a subset of the larger set, having one or more members, but fewer members than the larger set. In formal set theory, one possible type of subset of a set S, that is, an "improper subset", may comprise the complete set S. A "proper subset" of set S, however, is strictly contained in set S and excludes at least one member of set S.

In the context of the present disclosure, the phrase "entered instructions" refers to control instructions that can be entered by an operator at an operator interface on a computer host (as described subsequently) or instructions stored in or generated by a program, such as in memory that is accessible to a computer or logic controller circuit. The term "actuable" relates to a function that can be selectively performed, such as when initiated by a control signal. Similarly, the term "energizable" relates to a function or action that occurs when a device is energized, such as by switching on power to the device.

At least portions of the method of the present invention execute on a computer or other type of control logic processor, which may include a dedicated microprocessor or similar device. A computer program product used in an embodiment of the present invention may include one or more storage media, for example; magnetic storage media such as magnetic disk or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice the method according to the present invention.

It should be noted that the term "memory", equivalent to "computer-accessible memory" in the context of the present disclosure, can refer to any type of temporary or more enduring data storage workspace used for storing and operating upon image data and accessible to a computer system. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer is also considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

The apparatus and methods of the present invention help to resolve the problems experienced when using conventional, fixed-position AEC devices by providing an adaptable arrangement of individually addressable sensor devices in an AEC panel or other configuration. For example, this feature enables an AEC panel to be configured appropriately for the size and overall build of each particular patient and with consideration for the type of tissue that is being imaged in each case.

Figure 2A:
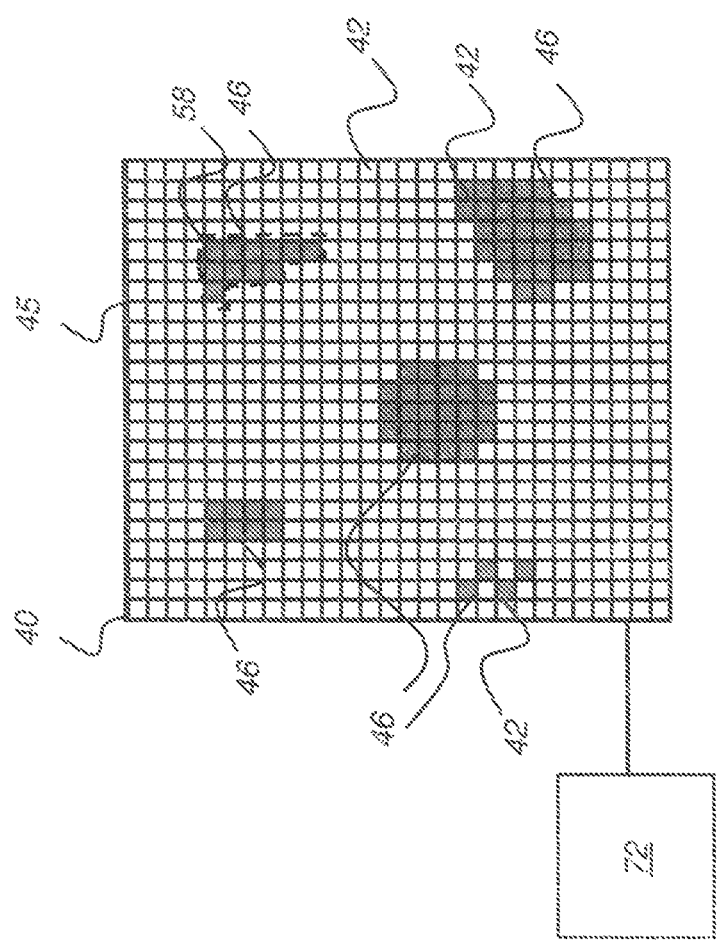
FIG. 2A is a plan view of an AEC apparatus with selectable sensor elements according to one embodiment of the present invention.

Referring to FIG. 2A, there is shown a configurable AEC apparatus 40 for sensing the level of ionizing radiation received according to one embodiment of the present invention. AEC apparatus 40 is configured as a two-dimensional array of sensor elements 42, arranged in rows and columns on a panel 45 in the embodiment shown. In the arrangement of FIG. 2A, each individual sensor element 42 is individually addressable to provide a measurement signal indicative of the amount of ionizing radiation that it receives. Cells that appear to be grayed in the example of FIG. 2A indicate sensor elements 42 that are enabled or addressed for obtaining the measurement signal; cells with white background indicate sensor elements 42 that are not enabled, that is, not addressed in this example. Each enabled (grayed) cell forms part of a composite radiation measurement region 46.

In the example of FIG. 2A, AEC apparatus 40 provides a large set comprising a plurality of sensor elements 42, here the product (m×n) elements, in an array wherein m is the number of rows and n the number of columns. Using the rectangular array grid pattern of FIG. 2A, for example, where sensor elements 42 are arranged in an array with 28 rows and 23 columns, the full set of sensor elements has 28×23=644 members. One or more smaller, proper subsets of this set are then selected to be addressed for providing measurement signals according to entered instructions. The selected composite radiation measurement region or proper subset in this example can have as few as two members, as many as 643 members.

The array arrangement of sensor elements 42 can vary significantly from the row/column arrangement of equal-sized components shown in FIG. 2A and other figures in this specification. Sensor elements 42 can utilize ion chamber sensing, as in conventional AEC devices, or may employ some other type of radiation sensing device. Neighboring sensor elements 42 may be substantially contiguous, as shown in FIG. 2A and in other exemplary figures of the present application, or may be spaced apart from each other, at consistent or variable spacing intervals. It can be appreciated that a grid of sensor elements extending fully across the length and width of detector 12 may be impractical, providing some elements that would seldom, if ever, be used for some detector 12 configurations. Thus, a more strategic placement of selectable sensor elements 42 in a two-dimensional array pattern can be used, depending on the type of imaging apparatus or type of detector that is employed. Sensor elements 42 can be of the same dimensions or may have different dimensions and shapes.

The measurement signals correspond to the amount of incident ionizing radiation received by the subset of sensor elements 42 that are addressed within an assigned radiation measurement area. Each selected proper subset is considered to be a composite radiation measurement region 46, and measurement signals are obtained from this proper subset. Each composite radiation measurement region 46 has a boundary 58, shown in dashed line form for only one of the composite radiation measurement regions 46 in FIG. 2A. An AEC controller circuit 72 responds to entered instructions to assign and define each composite radiation measurement region 46 and, when needed, to adjust its boundary by changing the proper subset of sensor elements 42, thereby either resizing or shifting the spatial position of composite radiation measurement region 46.

As is shown in FIG. 2A, the selected sensor elements 42 in each enabled composite radiation measurement region 46 may be substantially contiguous. Substantially contiguous sensor elements 42 are adjacent or "nearest neighbors", contiguous or touching along an edge of the sensing area, forming composite radiation measurement region 46 as a larger block or pattern. Alternately, neighboring sensor elements 42 in a composite radiation measurement region 46 can be substantially contiguous along a corner with respect to each other. Because sensor elements 42 are discrete components, there is typically some small amount of space needed between adjacent or contiguous sensor elements 42 in panel 45. Two sensor elements 42 of given height and width dimensions H and W can be considered to be substantially contiguous wherein the spacing between them is less than either value H or W, preferably less than half of either value H or W, and more preferably, when the spacing between does not exceed 0.1 times the smaller of H or W.

As FIG. 2A also shows, an AEC controller circuit 72 is coupled with the array of sensor elements in configurable AEC apparatus 40. AEC controller circuit 72 contains the logic for defining one or more composite radiation measurement regions 90, including spatial position and area or size, and for collecting measurement signals from the selected sensor elements 42. AEC controller circuit 72 may be packaged with the array of sensor elements or may be separately provided, as described in more detail subsequently. The collected measurement signals are then used to generate the output signal that is transmitted for control of x-ray generation from the x-ray source. The collected measurement signals may be combined in a number of ways, such as summing, averaging, or using some other combination method.

Figure 2B:
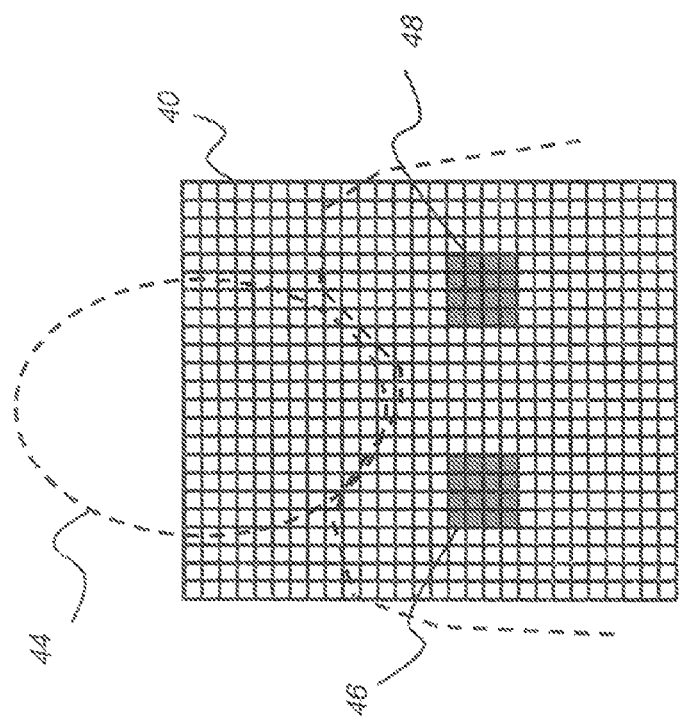
FIG. 2B is a plan view of an AEC apparatus with a selected pattern of composite radiation measurement regions.
Figure 2C:
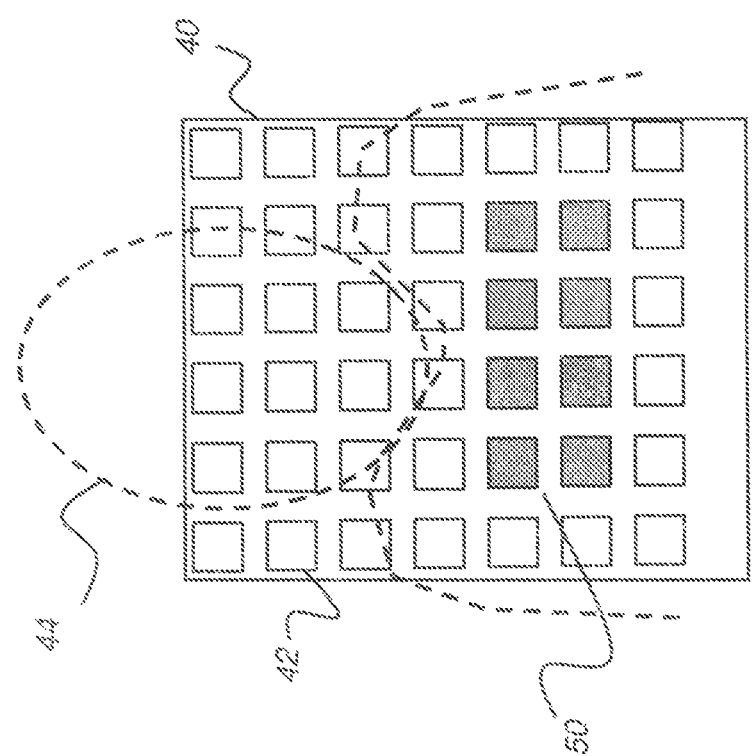
FIG. 2C is a plan view of an AEC apparatus with a single composite radiation measurement region selected.
Figure 2D:
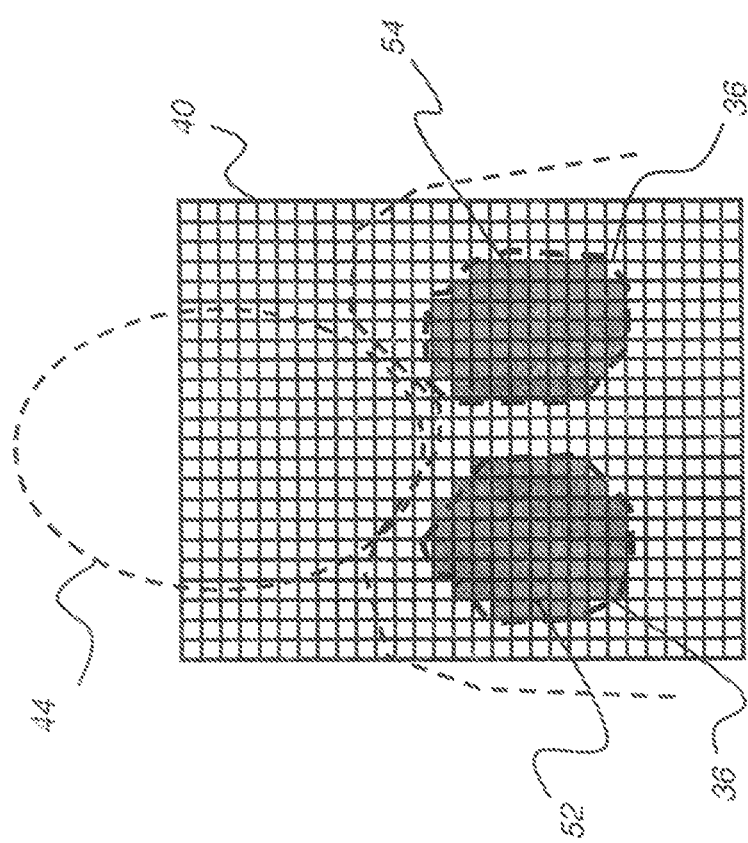
FIG. 2D is a plan view of an AEC apparatus with an alternate pattern of composite radiation measurement regions selected, configured to correspond to underlying tissue being imaged.
Figure 2E:
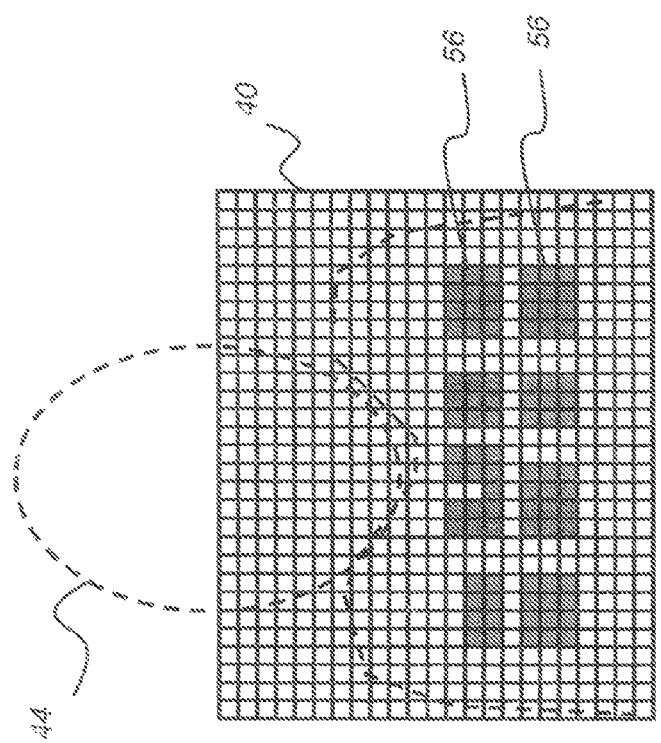
FIG. 2E is a plan view of an AEC apparatus with another alternate pattern of composite radiation measurement regions selected, with composite radiation measurement regions of different sizes.

FIGS. 2B-2F show various arrangements of the selected subset, as considered against an overlaid outline 44 of a patient or other subject, shown in dashed lines. In FIG. 2B, enabled sensor elements 42 are arranged in two composite radiation measurement regions 46 and 48. In FIG. 2C, enabled sensor elements 42 are grouped into a single composite radiation measurement region 50. Sensor elements 42 have a different size (area) and spacing in this embodiment from that shown elsewhere in the present application. FIG. 2D shows enabled sensor elements 42 arranged in composite radiation measurement regions 52 and 54 that approximate underlying organ tissue structures that are of interest. FIG. 2E shows an example of a distributed arrangement of composite radiation measurement regions 56 of different sizes and shapes. By way of comparison, FIG. 2F shows a conventional arrangement of fixed-position, fixed-size sensor elements 22, which can also be used in embodiments of the present invention, but often provide much less flexibility than other arrangements.

It should be noted that, in an alternate embodiment of the present invention, AEC sensor elements 42 can be arranged in other than the generally rectangular row-column matrix arrangement shown in FIGS. 2A-2E. For example, sensor elements 42 can be provided as separate composite radiation measurement regions of regular or irregular shape. Moreover, sensor elements 42 may be in the form of discrete elements, mounted together and generally provided within the same plane of panel 45. In such an embodiment, sensor elements 42 may be movable, positionable along a platen or other holding device, held in place magnetically or using hook-and-loop fasteners or other type of coupling device.

Imaging Apparatus

Figure 3A:
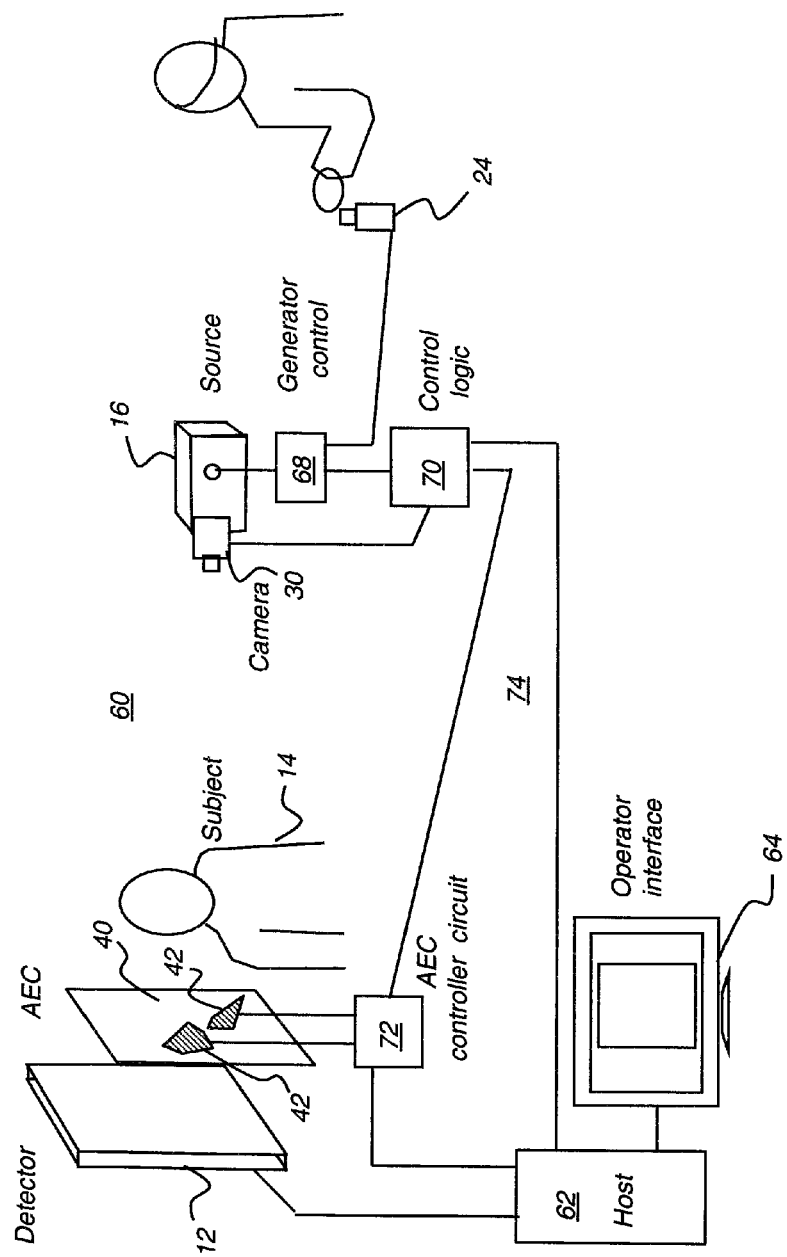
FIG. 3A is a block diagram showing components of a radiographic imaging apparatus using the AEC apparatus of the present invention with a wired transmission channel.
Figure 3B:
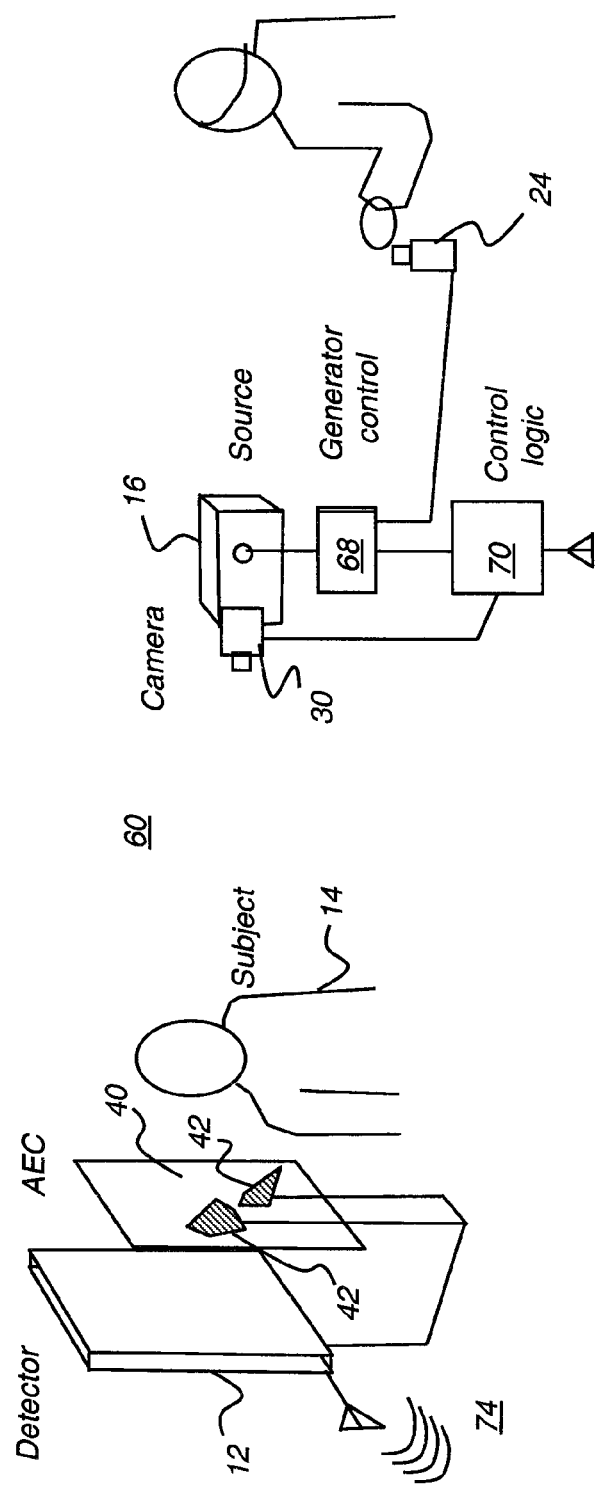
FIG. 3B is a block diagram showing components of a radiographic imaging apparatus using the AEC apparatus of the present invention with a wireless transmission channel.

By making the AEC device configurable to variations in patient build and to differences in types of tissue imaged, embodiments of the present invention enable the design of a more adaptive x-ray imaging apparatus that directs an appropriate amount of exposure for a particular image. The schematic block diagrams of FIGS. 3A and 3B show embodiments of an x-ray imaging apparatus 60 that provide this advantageous arrangement. It is noted that these block diagrams are in simplified form, are not drawn with intent to show actual scale, and show some components widely spaced apart with respect to the imaging axis in order to help simplify description. AEC components, for example, are typically spaced very close to the patient and to the detector in practice. Detector 12 can be any of a number of types of radiographic imaging detector, including a film cassette or other type of holder, a computed radiography (CR) detector, or a digital radiography (DR) detector. The embodiment shown uses a DR detector having an optional wire connection to a host computer 62. AEC apparatus 40 is typically positioned against or very near the surface of detector 12; FIGS. 3A and 3B extend this usual distance for better visibility of components relative to the following description.

FIGS. 3A and 3B show a number of functional control components that can be embodied in any of a number of alternative ways. For example, AEC controller circuit 72 can be a component that is integral to AEC apparatus 40 itself, or can be a separate component, or may be implemented as a function of detector 12, host computer 62, or some other component. Similarly, control logic circuit 70 can be combined with generator control 68 or may be implemented as a function of host computer 62 or some other suitable component. It can be appreciated by those skilled in the systems engineering and design arts that any number of arrangements for carrying out the functions of these control components are possible.

In the embodiment shown in FIG. 3A, as part of a sensing apparatus 73 that is actuable to configure the arrangement of sensor elements, host computer 62 connects to AEC controller circuit 72 that provides combined signals from the selected sensor elements 42 on AEC apparatus 40. An optional display 64 provides an operator interface for setup and selection or designation of enabled sensor elements 42, as described in more detail subsequently.

Still referring to FIG. 3A, a generator control 68 is energizable to initiate and terminate generation of the radiation signal from X-ray source 16. An optional control logic circuit 70 provides an interface between AEC controller circuit 72 and generator control 68. In one embodiment, control logic circuit 70 receives the combined signal from AEC controller circuit 72 and compares that against a threshold value to determine when to terminate the generation of radiation from X-ray source 16. In an alternate embodiment, wherein control logic circuit 70 is integral to host computer 62, host computer 62 performs the signal comparison and sends a terminating signal directly to generator control 68. A transmission channel 74 extends between the AEC controller circuit 72 and control logic circuit 70 for controlling the termination of x-ray generation by x-ray source 16. In the embodiment of FIG. 3A, transmission channel 74 is shown over a wire or cable, such as a fiber optic cable. In the embodiment of FIG. 3B, a wireless transmission channel 74 is used.

Turning now to FIG. 3B, in a wireless embodiment, the output signal from each of the enabled AEC sensor elements 42 is provided to on-board control logic in DR detector 12. This control circuitry is actuable to form a combined signal from these measurement signals and transmits the output signal to control logic circuit 70 for terminating the generation of X-rays.

From FIGS. 3A and 3B, it can readily be appreciated that a number of alternative arrangements are possible using either wired, including electrical or optical fiber connection, or wireless transmission of the combined signal that is generated from the individual AEC sensor element output signals. With the wired transmission channel 74 of FIG. 3A, the combined output signal can be an analog signal that is compared against a threshold value in generator control or control logic circuit 70. Alternately, a binary on/off signal can be provided based on comparing signal levels at the detector 12, at AEC apparatus 40, at AEC controller circuit 72, or at host computer 62. The wireless arrangement of FIG. 3B is better suited for generation of the combined signal as a digital value for transmission. It should also be noted that communication between AEC apparatus 40 and generator control 18 could be accomplished using wired or optical cable or wireless communication from the bucky or other component of the imaging system. Methods for combining the output signals from individual AEC sensor elements 42 can include averaging, weighting variability for particular AEC sensor elements 42, or threshold comparison directly with individual or summed output signals. As has been noted, various components shown, particularly AEC controller circuit 72, control logic circuit 70, host computer 62 and generator control 68 can be implemented in any of a number of ways. For example, a single hardware component can be used to perform all of the combined functions described.

Figure 4A:
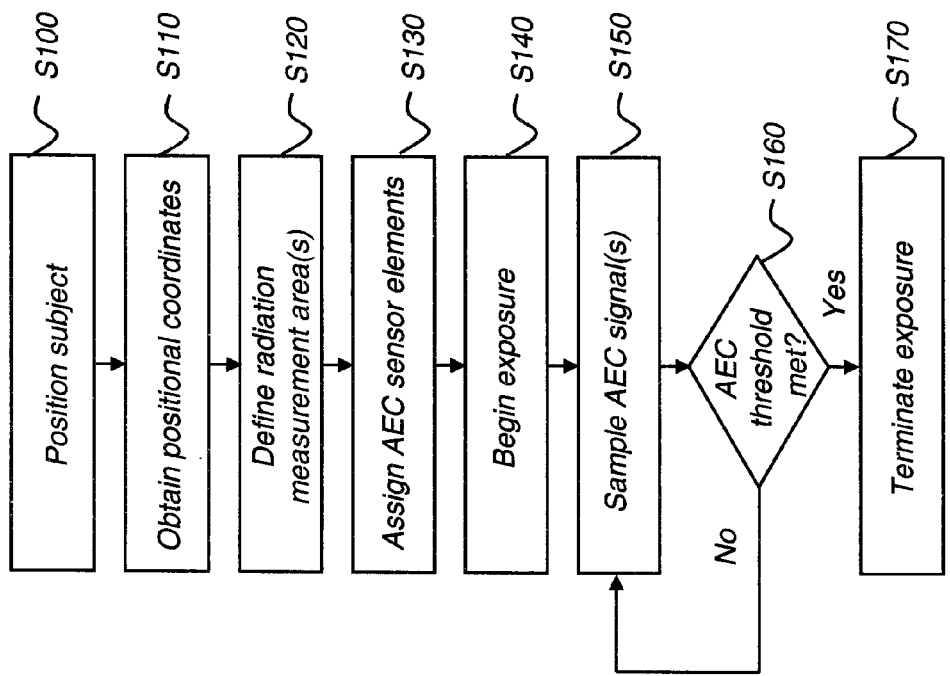
FIG. 4A is a logic flow diagram that shows a sequence of steps for determining when to terminate exposure using an embodiment of the present invention.

The logic flow diagram of FIG. 4A shows operational steps for terminating exposure using the AEC apparatus of the present invention. In a setup step S100, the subject is positioned in front of the detector and AEC apparatus. An obtain positional coordinates step S110 then obtains positional coordinate data that is indicative of the subject, or portion of a subject, that is to be exposed to radiation for obtaining an image. The positional coordinate data can be referenced to the subject and to the imaging detector. A define radiation measurement area step S120 then uses the positional coordinate data from step S110 to define a suitable radiation measurement area corresponding to the portion of the subject that is to be imaged.

Referring back to FIGS. 2D and 2F, for example, executing define radiation measurement area step S120 defines two desired radiation measurement areas 36, shown in bold dashed outline. In terms of relative spatial position, desired radiation measurement areas 36 correspond to those portions of the subject of most interest for radiation detection and measurement. A subsequent assign sensors step S130 then performs the actual mapping of desired radiation measurement areas 36 to sensor elements 22 or 42, depending on the sensor arrangement of the AEC apparatus in a particular embodiment.

Consistent with one embodiment of the present invention, the AEC device is highly adaptable for responding to measurement requirements. In the embodiment shown in FIG. 2D, for example, AEC apparatus 40 provides two composite radiation measurement regions 52 and 54 that correlate closely to desired radiation measurement areas 36 that were defined according to positional coordinate data. In one embodiment, outline 44 is displayed on an operator interface display, such as on display 64 (FIG. 3A). Outline 44 is obtained from a library of patient outlines, indexed by patient height, size, and other statistically obtained dimensional data. Composite radiation measurement regions 52 and 54 are then automatically calculated in step S130, defined based on information about the positional coordinate data obtained using outline 44 and, optionally, according to information on the type of exam and other factors.

In an alternate embodiment of the present invention, as shown in FIG. 2F, the capability for setting up composite measurement regions is not available. In this case, the conventional arrangement of AEC apparatus 40 allows selection and use of only a small number of sensor elements 22, each of fixed area and fixed position. When desired radiation measurement areas 36 are defined, an attempt is made to provide a suitable arrangement of sensor elements based on what is available. In FIG. 2F, the upper two sensor elements 22, having substantial overlap corresponding to desired radiation measurement areas 36, are assigned in step S130. The lower sensor element 22, because it has only peripheral portions corresponding to the desired radiation measurement areas, is not assigned in this example. A number of alternate approaches can be used for steps S110, S120, and S130, each described in more detail subsequently.

Continuing to follow the sequence of FIG. 4A, assign sensors step S130 determines which of the AEC sensor elements are enabled for use as part of composite radiation measurement regions 46, to be addressed for obtaining their measurement signals as output. This sets up the variable AEC sensor configuration. A number of alternate embodiments can also be used for assign sensors step S130, as described in more detail subsequently.

Continuing with the FIG. 4A sequence, automatically executed steps follow a begin exposure step S140. Step S140 initiates exposure, activating the generator that provides x-ray radiation. As exposure commences, a sampling step S150 automatically executes, obtaining the measurement signals by periodically or continuously addressing the selected AEC sensor elements 42. A comparison step S160 checks the obtained measurement signal level against a reference threshold value in order to determine if exposure should be terminated. If the measured AEC measurement signals do not yet meet the threshold signal value, sampling step S150 is again executed and comparison step S160 repeated, until the threshold is met and a termination step S170 is performed to end exposure.

It can be appreciated that the sequence of steps shown in FIG. 4A is exemplary and admits a number of variations for measuring exposure energy and determining when to terminate x-ray generation. Define radiation measurement area step S120, for example, can be performed in a number of ways, based on the type of image that is obtained. Additional information about the type of exam, patient condition, pediatric information, or other factors may be used to execute assign sensors step S130. Operator-entered values may be used to change the overall behavior of AEC apparatus 40. Alternately, default operation without operator interaction can be used. The method described with reference to FIG. 4A can be used with an imaging system that obtains multiple images using a sequential sequence of exposures in pulsed form and acquires a measurement signal during this process; alternately, the process shown in FIG. 4A can be used with a system that applies radiation continuously until a termination signal is received.

Obtain Positional Coordinates Step S110

As described with reference to the sequence of FIG. 4A, positional coordinate data is obtained for the subject, so that it can be used to define and configure the radiation measurement area that is used. The positional coordinate data itself can take any of a number of forms and relevant coordinate data can be stored in a computer-accessible memory, for example. Methods and approaches for obtaining and storing positional data that relate to components of an imaging system are known to those skilled in the imaging arts.

Figure 4B:
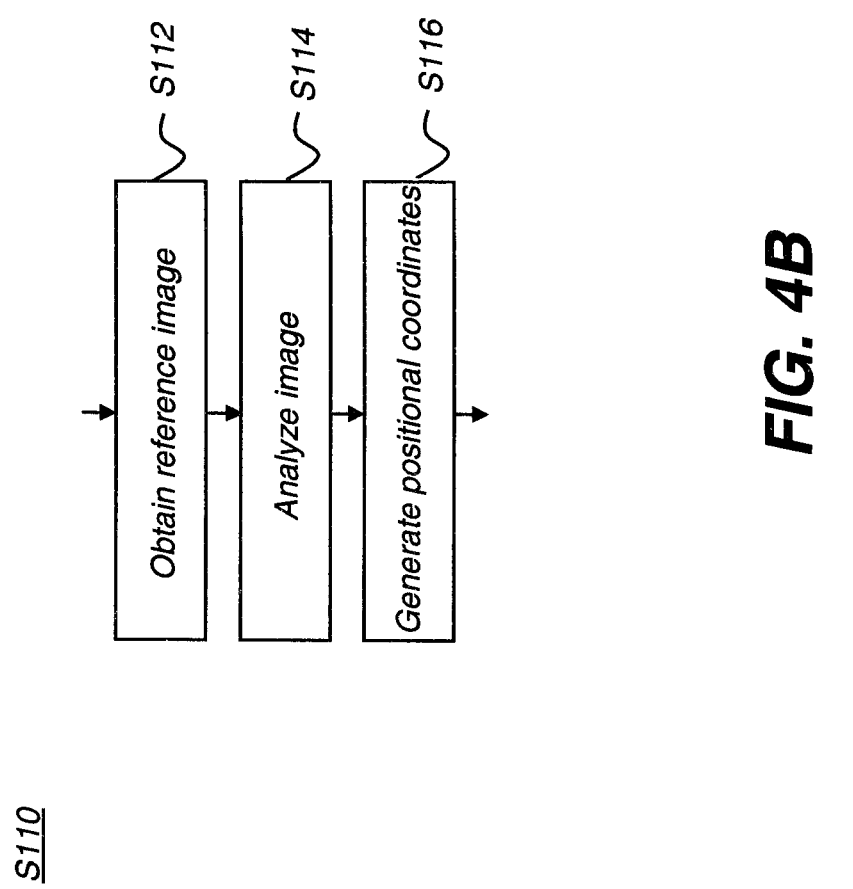
FIG. 4B is a logic flow diagram that shows a sequence of steps for obtaining positional coordinates according to an embodiment of the present invention.

FIG. 4B shows a sequence of steps for obtain positional coordinates step S110 according to an embodiment of the present invention. An optional reference image capture step S112 obtains an image of the subject that can be used as a reference to determine which AEC sensor elements to address for obtaining an output signal for the x-ray image. Using the configuration shown in FIG. 3A or 3B, for example, a camera 30 is actuable to obtain a reference visible light image of the subject for use in determining which AEC sensor elements should be enabled. Camera 30 is aligned with x-ray source 16 in these embodiments. In an alternate embodiment using a DR imaging detector, an initial momentary radiation pulse is generated from x-ray source 16 for generating reference image data from the detector, providing the positional coordinate data that will be used in configuring AEC sensor enablement. Advantageously, energy from this momentary radiation pulse can be added to subsequently provided radiation in order to obtain the exposure image from the detector. In an alternate embodiment, an optional microwave scanner 32 is used to obtain an outline image of the subject. When the optional image is obtained in step S112, an analyze image step S114, executed on the host processor, for example, then analyzes the image data that is obtained in reference image capture step S112. A generate positional coordinates step S116 then generates the needed positional coordinates for indicating the portion of the subject that is to be exposed to radiation and for defining one or more radiation measurement areas. The image data can also be used to help in operator configuration of AEC sensors on display 64, as described in more detail subsequently.

When a radiation pulse is used as part of step S112, an outline of the patient can be readily obtained when using the grid arrangement shown in FIG. 2A. By evaluating the measurement signals, sensor elements 42 subjected to radiation that is not obstructed by the subject can be clearly distinguished from sensor elements 42 that lie behind the subject, relative to the x-ray source 16.

In an alternate embodiment, information about the patient, provided by the operator or from patient medical history or other source, is used to obtain positional coordinate information. For example, the relative build of the patient, the type of exam, and relevant data from earlier exams can be used to generate or to modify default positional coordinate data. A standard profile can be provided for outline 44 (FIGS. 2B-2F), displayed to an operator as a check on calculated results.

Automatic generation of positional data can be fairly straightforward where the position of the patient is somewhat fixed relative to the imaging detector and AEC or other sensing device. Assumptions on relative position can then be made with reasonable likelihood for anatomy to be imaged in such a case. With more portable x-ray systems, however, patient positioning relative to the detector can vary from one exam to the next, so that additional positioning information is often helpful. In one embodiment, manual entries by a technician are used to indicate patient position or to adjust default position or sizing for radiation sensing.

Assign Radiation Measurement Area Step S120

Referring back to FIG. 4A, step S120 for defining the radiation measurement area can be performed in a number of ways, based on the results of step S110. Automatic assignment can be performed, in which the host computer 62 or other processor designates an area within which one or more sensor elements 42 are desired. In an alternate embodiment, the assigned radiation measurement area is defined by the technician, such as by tracing out the area on an operator interface, as described in more detail subsequently.

In one embodiment of the present invention, step S120 that defines the radiation measurement area and step S130 that assigns AEC sensor elements are executed in a single operation. When using the conventional AEC apparatus of FIG. 1B, for example, there is no flexibility in determining the size (area) or position of sensor elements 22; these components are of fixed size and position. This simplifies the sequence of FIG. 4A, but is a limited solution in terms of flexibility and adaptability to specific exam requirements for a particular patient. In an alternate embodiment, when using an apparatus that allows configurable size and position of radiation sensing areas by grouping two or more sensing elements in a proper subset selected from the full set of available sensing elements, steps S120 and S130 can be considered separately. Step S120 defines the desired area for radiation measurement; step S130 then provides assignment of specific sensors corresponding to the desired area, in one embodiment allowing for operator adjustment in particular cases.

In an alternate embodiment, a technician can define the desired radiation measurement area by using a pointer or indicator when standing by the patient, as described in more detail subsequently.

Assign Sensors Step S130

Assign sensors step S130 can be executed in a number of ways. Consistent with one embodiment, the assignment is executed using entered instructions on display 64 or from instructions entered using touch sensors on the AEC apparatus 40 itself, as described in more detail subsequently. Consistent with an alternate embodiment, programmed assignment allows a default set of composite radiation measurement regions 46 to be automatically used unless changed by an operator. Pre-programmed instructions, obtained from a computer-accessible memory or storage medium, are executed in order to apply logic processing to the problem of AEC sensor element selection, such as on host computer 62 (FIG. 3A).

Thus, for example, computer logic is used to configure an arrangement of AEC sensor elements such as those shown in the examples of FIGS. 2A-2F. The arrangement that is selected can be from a pre-stored pattern, one of a set of possible patterns for selection, or computed from information derived about the type of imaging exam that is to be performed and about the outline of the patient, computed from an obtained image or obtained from a stored outline approximating patient height and size, as described earlier with respect to step 110. It is noted that assignment or enablement of AEC sensor elements refers to whether or not the elements are addressed for providing their respective output signals during exposure. All sensor elements 42 may be provided with power for operation, but only those that are addressed provide their measurement signals as output for exposure measurement. In one embodiment, assigned AEC sensor elements are identified and their addresses listed in a memory buffer, which is then used to access measurement signal information from each listed element periodically or continuously during exposure.

Consistent with one embodiment, assign sensors step S130 also optionally includes setup procedures for configuring the response of one or more of the sensor elements 42. Adjustments can be made to adjust the sensitivity level or to set an exposure threshold in mAs or other unit, for example. This setup relates to the type of measurement signal provided from each sensor element 42 and to how the respective measurement signals may be combined and used in subsequent processing. In an alternate embodiment, no operator adjustment is needed and aspects of sensor element 42 grouping and response are automatically assigned and used unless changed.

Selection of Subset

Figure 5A:
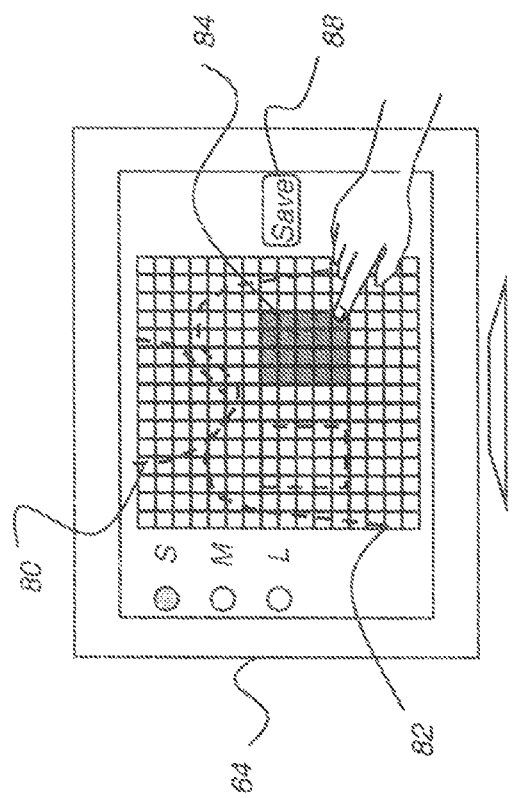
FIG. 5A is a plan view of a display showing technician configuration of an AEC apparatus.

Embodiments of the present invention allow the technician to select, by way of entered instruction, which sensor elements 42 of AEC apparatus 40 are used for a radiographic image. In the embodiment shown in FIG. 5A, display 64 is used as a type of control console for sensor element 42 selection. An optional outline image 80 of the patient or other subject is overlaid over an image 82 of AEC apparatus 40, aligned with corresponding sensor elements on the AEC apparatus. In the embodiment shown, patterns of predefined composite radiation measurement regions 84 are presented for operator selection, such as using a touchscreen selection as shown or using a mouse, joystick, or other suitable pointer. A Save command 88 enables the selected sensor elements 42 and allows the technician to proceed with the imaging process. With this arrangement, for example, the technician is presented with a small number of options, such as Patient size: Large, Medium, or Small in a menu selection or using a radio button 92 on the operator interface. Current view information, such as information on anatomy to be imaged, projection information, and patient position, can also be entered or obtained from setup data. Selection in this field then adjusts the composite radiation measurement region 84 arrangement automatically, without the need for visualization or use of positioning by the technician. Alternately, technician adjustment may be permitted.

In one embodiment, the selection of the subset of sensor elements for assign sensors step S130 employs information about the patient that is available from other networked sources, such as age and height or other data from a patient record, or from image type and setup information or from previous x-rays, stored in a DICOM system or other database. Auxiliary information about the type of the image obtained and the power levels used can also indicate patient size. Thus, for example, information about patient size can be derived indirectly or otherwise obtained and used for specifying the size (area) and position of composite radiation measurement region 46.

FIG. 5B shows a more interactive arrangement that gives the technician additional flexibility for making sensor element 42 selections and thereby adjusting the boundary, position and size, of the composite radiation measurement region. Here, the position and boundary of composite radiation measurement region 84 is traced out by the technician, such as using a touchscreen as shown. The technician can outline an area to select all sensor elements 42 within the outline. Optionally, the technician can separately enable or not use any individual sensor element 42 in the array. The technician can also perform operations that spatially shift the position of one or more composite radiation measurement regions 84, such as moving composite radiation measurement region 84 upwards or downwards according to patient height or build. This can be done using "drag and drop" manipulation utilities, keyboard commands, or other instruction entry. Resizing of composite radiation measurement region 84 may also be executed by the technician. It can be appreciated that any of a number of user interface utilities could be used to adjust position or size of composite radiation measurement regions 46.

Also shown in FIG. 5B is an entry window 90 for the technician to specify the exposure level or signal level threshold for a particular composite radiation measurement region 84 or, in one embodiment, individually for each of the two or more sensor elements 42 within composite radiation measurement region 84. In one embodiment, window 90 displays when the technician configures or points to a particular composite radiation measurement region 84, allowing value entry or adjustment. Window 90 can alternately be used for entering data related to adjustment of AEC calibration values.

Figure 5C:
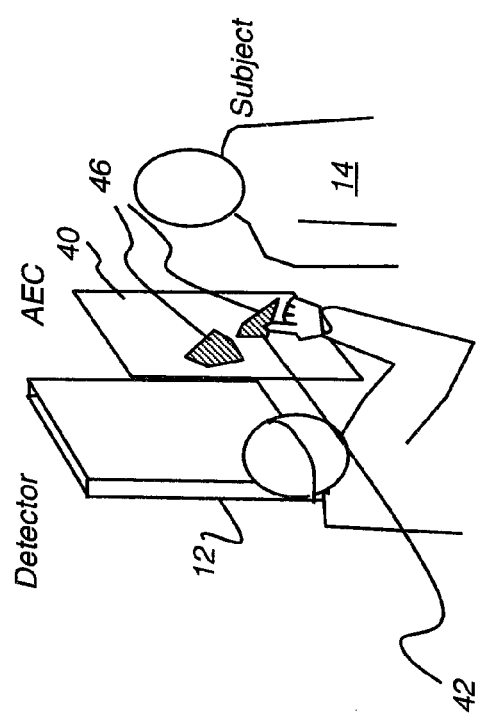
FIG. 5C is a perspective view showing technician selection of AEC sensor elements directly on the AEC apparatus itself.
Figure 5D:
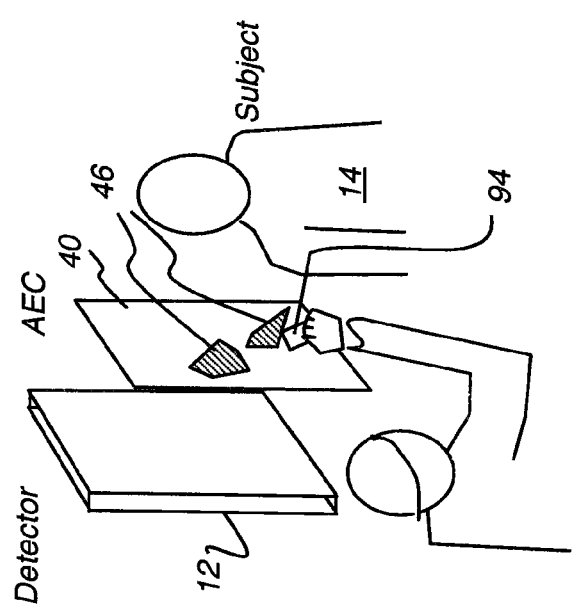
FIG. 5D is a perspective view showing technician selection of AEC sensor elements using an exposure switch.

The perspective view of FIG. 5C shows an alternate arrangement in which the technician selects the appropriate AEC sensor elements 42 on AEC apparatus 40 itself to form composite radiation measurement regions 46. Touch-sensitive elements (not shown) are provided to accept technician instructions on which underlying AEC sensor elements 42 are enabled. An audible beep or other indication is provided to verify selection of each sensor element 42. In one embodiment, a manual switch setting on AEC controller circuit 72 (FIG. 3A) is used by the technician to select which sensor element 42 is enabled. In an alternate embodiment, one or more of the AEC sensor elements 42 is movable, magnetically coupled to the surface of AEC apparatus 40.

Figure 1B:
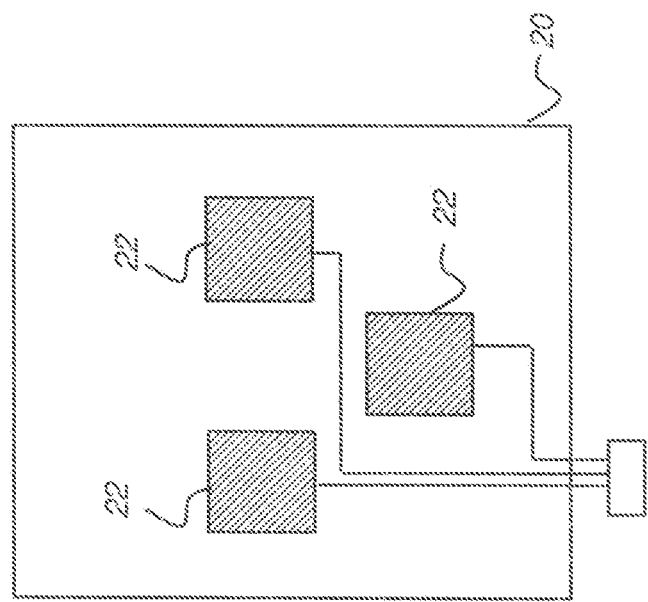
FIG. 1B is a plan view of an AEC apparatus having multiple sensor elements.

In yet another embodiment, an x-ray console could be utilized as the operator interface tool for AEC apparatus 40 setup. In one embodiment, as described earlier, a patient size setting is first performed by the operator, which simply adjusts the distance between sensor areas of apparatus 40 that will be used, thereby configuring AEC apparatus 40. The overall pattern of FIG. 1B is still used as a starting point; however, the technician or other operator can make corresponding changes to the subset grouping and position of AEC sensor elements to form suitable composite radiation measurement regions. This enables the technician to utilize an existing operator console interface in order to specify the desired signal level for x-ray termination.

Referring to the perspective view of 5D, there is shown an embodiment in which an exposure switch 94 or some other device is used as a type of hand-held pointer for defining the radiation measurement area (step S120 in FIG. 4A) and for positioning and sizing each composite radiation measurement region 46 on AEC apparatus 40 (step S130 in FIG. 4A). In one embodiment, placing and holding exposure switch 94 at a desired position adjusts the location and size of the corresponding composite radiation measurement region. Alternate pointing devices can be used. Related embodiments analyze and use technician gestures or audible commands for positioning and sizing composite radiation measurement regions 46. In one embodiment, the technician indicates, on the operator interface, which composite radiation measurement regions 46 to resize or to move. Then, a pointing device or technique of some type is used in order to reposition or resize the indicated composite radiation measurement region 46.

Consistent with an embodiment of the present invention, the position of each composite radiation measurement region 46 can be maintained regardless of the angle of orientation of detector 12 within the plane. Alternately, the composite radiation measurement regions 46 can be configured to rotate along with rotation of detector 12.

In general, where there are multiple composite radiation measurement regions 46, these regions are non-overlapping. However, there may be some overlap of boundaries between two composite radiation measurement regions 46 in various arrangements.

Consistent with one embodiment, information about the configuration of AEC apparatus 40 that is used for patient exposure is saved and stored as part of the DICOM metadata for the image.

It should be noted that, due to possible delays resulting from noise or other transmission problem, wireless communication can be less effective for transmitting commands and may not be error-proof in some environments. In one embodiment, a supplemental default timeout is applied to help reduce the likelihood of excessive exposure. This timeout value can be adjusted for variables such as patient size, imaging type, or other factors.

It should be noted that while the present description and examples are primarily directed to radiographic medical imaging of a human patient or other subject, the apparatus and methods of the present invention can also be applied to other radiographic imaging applications. This includes applications such as non-destructive testing (NDT), for which radiographic images may be obtained and provided with different processing treatments in order to accentuate different features of the imaged subject.

Display of Sensor Element Position

Embodiments of the present invention assist the technician by identifying the positioning of AEC sensor elements relative to the subject to be imaged, using an image forming apparatus. This identification can be done in a number of ways. Referring to the plan view of FIG. 6A, there is shown display 64 that serves as an image forming apparatus, having image 82 that represents the subject, such as an outline image or a still or moving image of the patient. Each sensor element 96 is also displayed, referenced to the subject in the example of FIG. 6A.

Figure 6B:
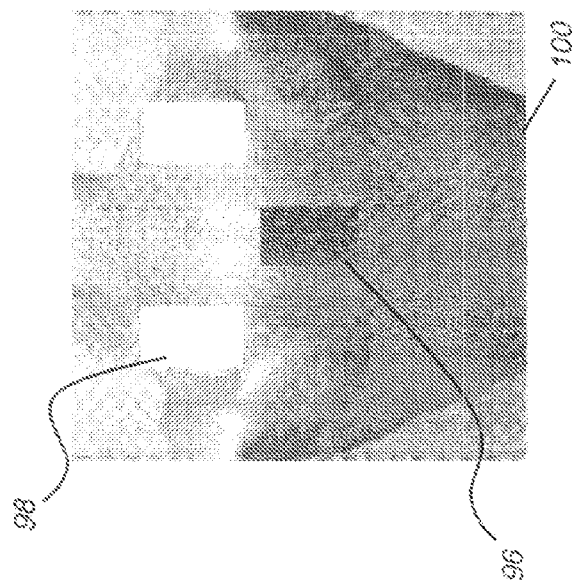
FIG. 6B is a plan view showing display of AEC sensor position by projecting an image onto the patient.
Figure 6A:
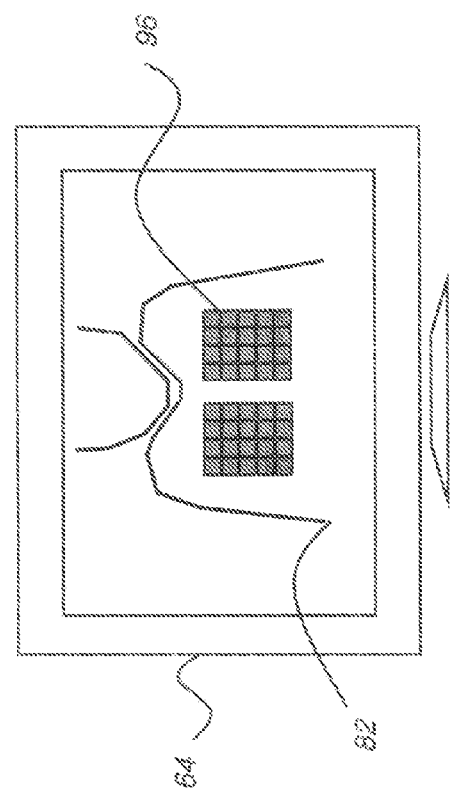
FIG. 6A is a plan view showing display of AEC sensor position on a display monitor.

Alternately, as shown in FIG. 6B, the relative position of sensor element 96 can be displayed by projection, so that the outline or area of sensor element 96 is highlighted directly on the patient or other subject 100. In the example of FIG. 6B, the lower sensor element 96 is addressed or enabled for use and appears in a color indicating this status. Two other sensor elements 98 are available, but are not currently addressed or enabled for use; thus, these unused sensor elements 98, although their position is identified, appear in a different color.

Figure 7:
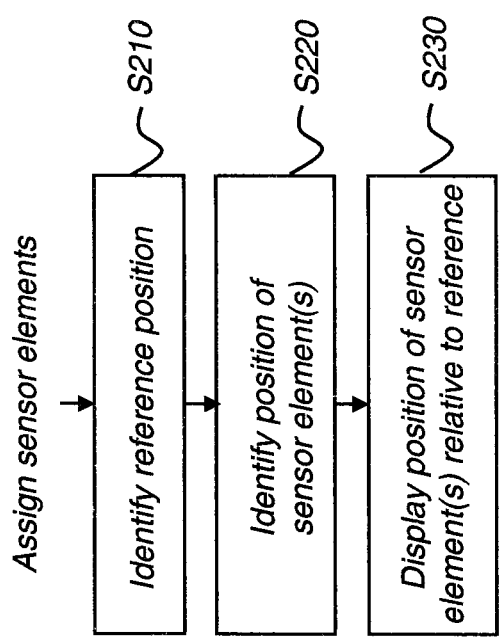
FIG. 7 is a logic flow diagram that shows a sequence for indicating the position of a radiation energy sensor element.
Figure 8:
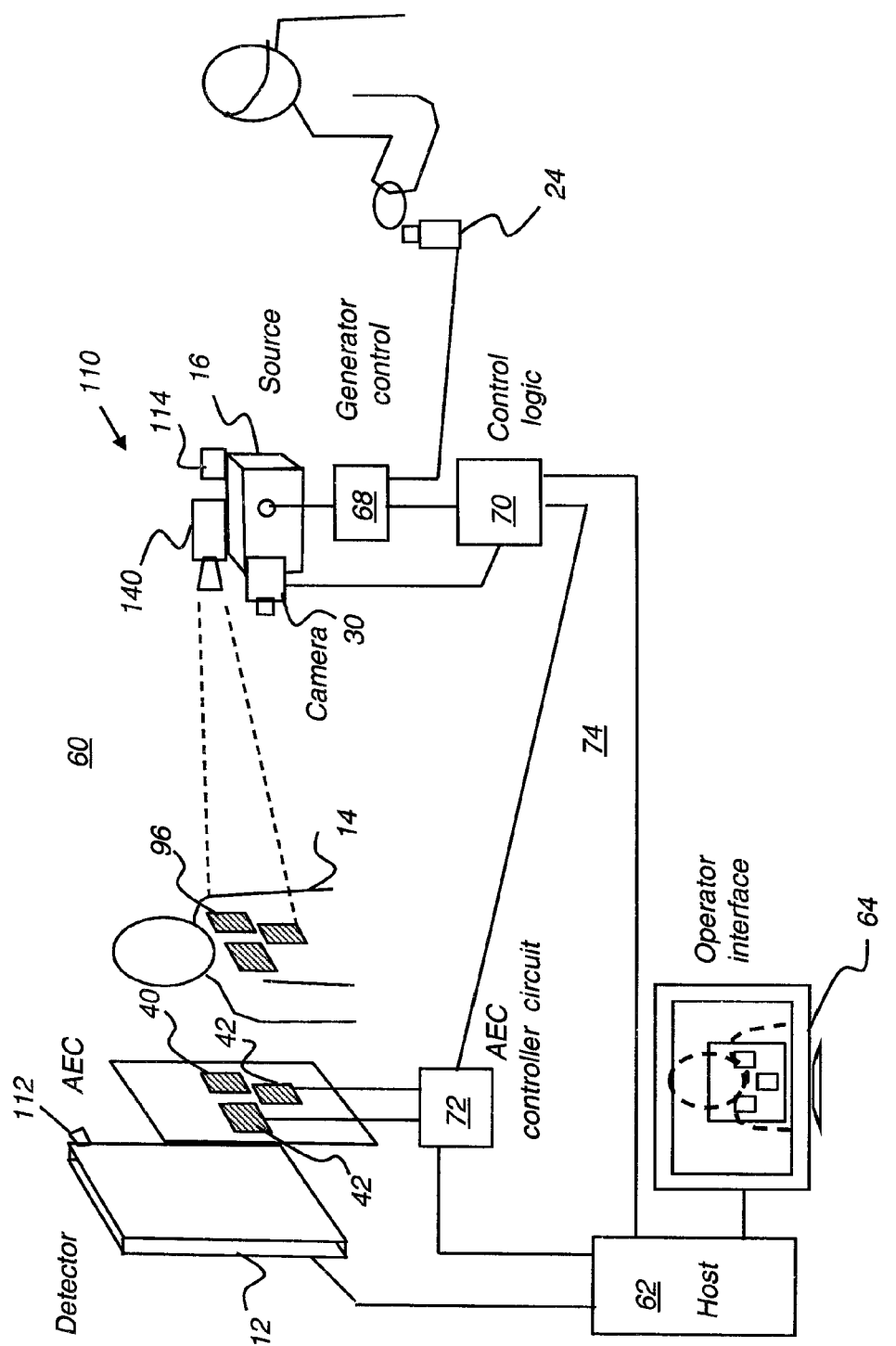
FIG. 8 is a schematic block diagram that shows components of a radiographic imaging apparatus using AEC apparatus and apparatus for indicating the position of AEC sensor elements.

The logic flow diagram of FIG. 7 shows the sequence of steps used for display of sensor elements according to an embodiment of the present invention. FIG. 8 shows a schematic diagram with components of the radiographic imaging system and a position sensing apparatus 110 that may be used in determining and indicating energy sensor element position.

As a prerequisite to the sequence of FIG. 7, one or more sensor elements is assigned or enabled for use with the current image, as described previously. A reference identification step S210, obtained using position sensing apparatus 110, defines and identifies a reference position on the subject that serves as a basis for determining the relative spatial coordinates of the assigned sensor element or elements (and, optionally, of one or more sensor elements that may be available but are not assigned) and used for subsequent display. Consistent with one embodiment of the present invention, the reference position relates to part of the subject 14 that is to be imaged, so that positioning of the sensor elements is determined relative to the outline of the subject or relative to some other reference location on or within the subject, for example. In an alternate embodiment, the reference position alternately relates to the imaging detector 12.

Position sensing apparatus 110 can include a number of components that are used to determine the relative spatial location of various components of imaging apparatus 60 that lie in the path of x-ray radiation. In the embodiment of FIG. 8, camera 30 and its associated control logic circuit 70 are part of position sensing apparatus 110, used to provide positioning information by obtaining and analyzing an image. Other arrangements of sensors, emitters, and reflectors can be used as part of position sensing apparatus 110 for obtaining related reference position data.

Continuing with the sequence of FIG. 7, the reference position that is identified in step S210 provides at least one fixed point relative to the subject from which other points can be identified for locating AEC sensor elements for an exposure. This reference position can be fixed by the installation itself, as described subsequently. This reference point can alternately be obtained, for example, from a marker or other element that is positioned in the field of view of a camera (FIG. 8), such as an outline of a device, for example. The reference position can be detected using a reflected light signal or using an emitted signal, such as a radio-frequency (RF) signal emitted from positions on a bucky or other holder, or from positions on a detector, on an AEC panel, or on the subject. The signal can alternately be emitted from an emitter that is coupled to the x-ray source 16, with the signal reflected back or detected at the reference device.

A number of methods are practiced for identifying the location of detectors that are used in radiographic imaging. For example, commonly assigned U.S. Pat. No. 7,806,591 entitled "ALIGNMENT APPARATUS FOR IMAGING SYSTEM USING REFLECTIVE ELEMENT" to Wang et al., incorporated herein by reference, describes the use of a light source and reflective elements for alignment of the x-ray signal to the detector; similar techniques using light or other emitted electromagnetic signal, combined with tools such as with triangularization, can also be used as part of position sensing apparatus 110 to identify a reference position, in conjunction with camera 30 (FIG. 8), using methods known to those skilled in the position-sensing arts. FIG. 8 shows a light source 114 for emitting a light signal and one reflector element 112 that can be used for this purpose.

Alternately, the reference position may be fixed according to the spatial arrangement of components installed as part of x-ray system 10. Thus, for example, sensor elements 96 may always have the same position within the imaging system, such as having fixed positions relative to detector 12, for example.

Following reference identification step S210, a sensor element positioning step S220 executes. Step S220 relates the position of each assigned exposure sensor element to the reference or subject position information obtained from step S210. Step S220 can be executed in a number of ways, depending on how the position of the sensor elements themselves is known. In one embodiment, for example, the position of the subject is the reference position. The position of detector 12 relative to the subject is then determined and, accordingly, used for relating the positions of one or more sensor elements to the reference position from step S210. In another embodiment, the outline of the imaging detector 12 provides the reference position and additional information from sensor element positioning step S220 is used to relate the positions of sensor elements to the detector.

Still continuing with the sequence of FIG. 7, a display step S230 is executed for displaying the identified position of the radiation energy sensor elements relative to the reference position using an image forming apparatus. In the context of the present invention, the "radiation energy sensor element" is a device that is used to indicate and control the amount of radiation that is received by the subject.

In one embodiment, as described previously with respect to FIG. 6B and also shown in FIG. 8, a projector 140 is the image forming apparatus, used to form an image that displays the identified position for radiation energy sensor elements. The projected image can be formed on subject 14 or, where the subject is not in position, on the surface of imaging detector 12. Projector 140, shown mounted on the x-ray source in FIG. 8, may be a pico-projector, such as a Pico Projector Display from Microvision Inc., Redmond, Wash., USA, or a Micro Projector from AAXA Technologies, Inc., Santa Ana, Calif., for example. Image forming devices such as these are advantaged for a number of reasons, including small size, low weight, and low power requirements. These small-footprint projectors, currently used in cell-phone and other highly portable electronic devices, scan one or more low-power solid-state light sources, such as light-emitting diodes (LEDs) or lasers onto a display surface. This type of projector employs a small number of optical components for projection over a range of distances. The solid-state light source itself can typically be turned on and off rapidly as needed, so that power is consumed only for those image pixels that are projected. This allows the display device to operate at low power levels, so that battery power could be used for projector 140. Alternate embodiments use other types of electronic imaging projectors as image forming apparatus, such as those that employ a digital micromirror array such as the Digital Light Processor (DLP) from Texas Instruments, Inc.; an array of micro-electromechanical grating light valves, such as the Grating Light Valve (GLV) device from Silicon Light Machines, Inc.; or a liquid crystal device (LCD) including a Liquid Crystal on Silicon (LCOS) device.

Where lasers are used as illumination sources in projector 140, additional measures can be taken to minimize incidence of coherent laser light to the eyes of the patient or technician. Very low power lasers would be used, at scanning rates that deliver only a very small amount of light intensity at any point. A diffusive element may be provided in the light path, for example, to provide some scattering of the laser light, reducing intensity with little or no effect on the quality or utility of the projected image. Various types of light-emitting diodes (LEDs) or other low-power solid-state light sources could alternately be used, such as organic LED (OLED) devices.

The image that is projected by projector 140 can take any of a number of forms and may include an outline of the position of sensor elements or may include one or more reference marks that indicate the position of the sensor elements. Different colors may be used in order to indicate assigned or un-assigned sensor element status. The projected image(s) may blink on and off or trace an outline to indicate sensor element position.

Projector 140 is positionally associated with x-ray source 16, so that it has a known spatial position relative to the source and can be coupled to x-ray source 16 by mounting it in a number of ways, for example. In one embodiment, projector 140 mounts on the side of collimator or boom mechanisms. Alternately, projector 140 mounts on the inner side of the collimator of the x-ray source. A beamsplitter or movable mirror that is internal to the x-ray source housing could alternately be used for directing the projection image from within the x-ray source housing.

As shown in FIG. 8 and described previously with reference to FIG. 6A, the position of radiation energy sensor elements can also or alternately be displayed on a display monitor, such as display 64 as another type of image forming apparatus. This display can show an image or an outline of the patient or other subject, or may show the outline of other reference locations on AEC apparatus 40 or on imaging detector 12.

It can be appreciated that there are a number of ways for obtaining positional coordinate data in an imaging apparatus, including methods that use light, RF signals, ultrasound, or other signal types.

It is noted that while the present description and examples are primarily directed to radiographic medical imaging of a human patient or other subject, the apparatus and methods of the present invention can also be applied to other radiographic imaging applications. This includes applications such as non-destructive testing (NDT), for which radiographic images may be obtained and provided with different processing treatments in order to accentuate different features of the imaged subject.

Obtaining Automatic Exposure Control Data from a DR Panel

Figure 9:
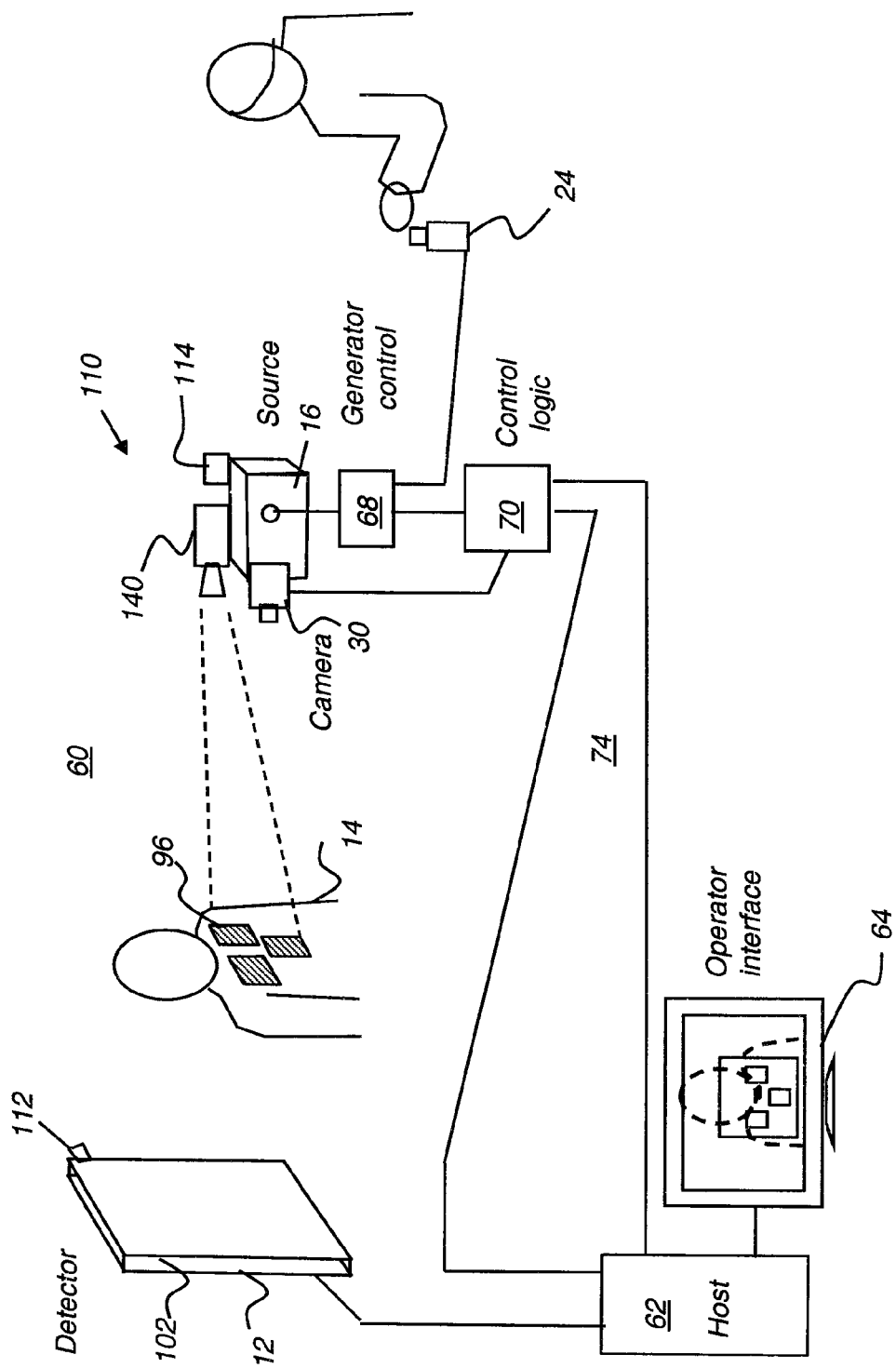
FIG. 9 is a schematic block diagram that shows components of a radiographic imaging apparatus using a DR detector to obtain automatic exposure control information.

Embodiments of the present invention provide automatic exposure control without the use of a separate AEC apparatus 40. Referring to FIG. 9, there is shown X-ray imaging apparatus 60 using DR detector 12 for obtaining automatic exposure control information and for providing a signal for terminating exposure.

Various approaches have been proposed for utilizing a DR panel for AEC sensing as well as for imaging. The solution proposed in U.S. Pat. No. 6,404,851 entitled "Method and Apparatus for Automatic Exposure Control Using Localized Capacitive Coupling in a Matrix-Addressed Imaging Panel" to Possin et al., for example, adapts a DR panel used for mammography for this purpose, obtaining a capacitively coupled signal along one or more existing data signal lines extending the full length or width of the DR panel. Other approaches, such as that shown in U.S. Pat. No. 7,368,724 entitled "Imaging Method and Apparatus with Exposure Control" to Morii et al., fabricate the DR panel itself with added AEC sensor detection areas. Even though such methods have been proposed, however, selecting and optimizing the AEC sensor assignment for a particular image or patient have not been suitably addressed.

Figure 10:
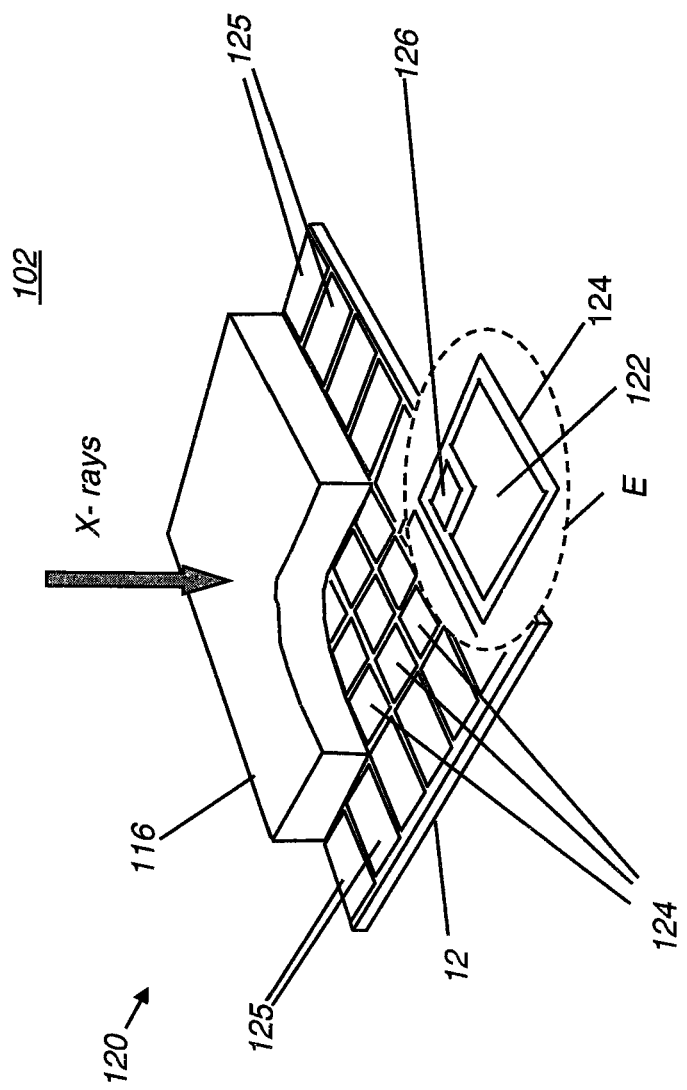
FIG. 10 is a partial cutaway perspective view showing components of a portion of a digital radiographic detector.

To appreciate how DR detector 12 can be used for this purpose, it is instructive to review the overall composition and operation of DR detector 12. The perspective view of FIG. 10 shows a partial cutaway view of a small edge portion of a DR panel 102 of the indirect type in which an intermediate scintillating element converts incident X-rays to visible-light photons which are then sensed by a light-sensitive image-sensing element. A scintillator screen 116 responds to incident x-ray radiation by generating visible light that is, in turn, detected by a flat panel detector (FPD) 12. DR panel 102 has a two-dimensional array having many thousands of radiant-energy sensing elements 120, typically organized as radiation sensitive imaging pixels 124, that are arranged in a matrix of rows and columns and are connected to readout element 125. As shown at enlarged section E, each pixel 124 has one or more sensors that provide a signal corresponding to the radiant energy received, broadly termed photosensor elements 122, such as a PIN diode or other light-sensitive component. Each pixel 124 also has an associated switching element 126 of some type, such as one or more thin film transistors, or TFTs. To read out image information from the panel, each row of pixels 124 is selected sequentially and the corresponding pixel on each column is connected in its turn to a charge amplifier (not shown). The outputs of the charge amplifiers from each column are then applied to other circuitry that generates digitized image data that can then be stored and suitably image-processed as needed for subsequent storage and display.

Figure 11:
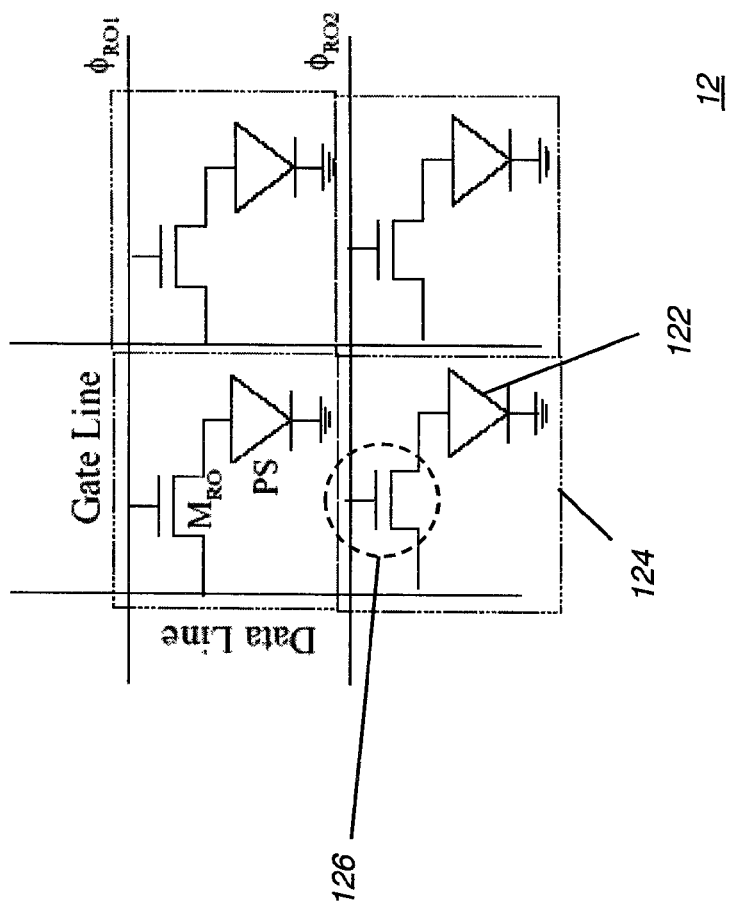
FIG. 11 is a schematic view of components in an exemplary image-sensing array of a panel used for digital radiographic imaging

FIG. 11 shows a schematic view of components in an exemplary image-sensing array of DR panel 102 used for DR imaging. In one basic embodiment, pixel 124 consists of at least one photoelectric conversion device or photosensor (PS) element 122, shown as a photodiode in FIG. 11, and at least one switching element 126, shown as a type of solid-state switch, $M_{RO}$.

Examples of photosensor elements 122 used for providing pixels in image sensing arrays include various types of photoelectric conversion devices such as photodiodes (P-N or PIN diodes), photo-capacitors (MIS), or photoconductors. Examples of solid-state switching elements used for signal read-out include MOS transistors, bipolar transistors and p-n junction components.

In order to obtain image data from DR panel 102, readout elements 125 address entire rows or columns of pixels 124 at a time, recording the sensed signal level from each individual pixel and using this data to form the visible image. Conventional operation of the array of DR panel 102 for obtaining image data basically consists in the steps of (i) initializing the array of pixels 124, such as by resetting all of the pixel values to zero or other reset state, (ii) exposing the array to the light radiation excited by X-rays, during which exposure each pixel accumulates charge indicative of the radiation it receives; and (iii) reading the signal value at each pixel of the array using a multiplexed signal-reading sequence that addresses pixels row by row or column by column.

Figure 12:
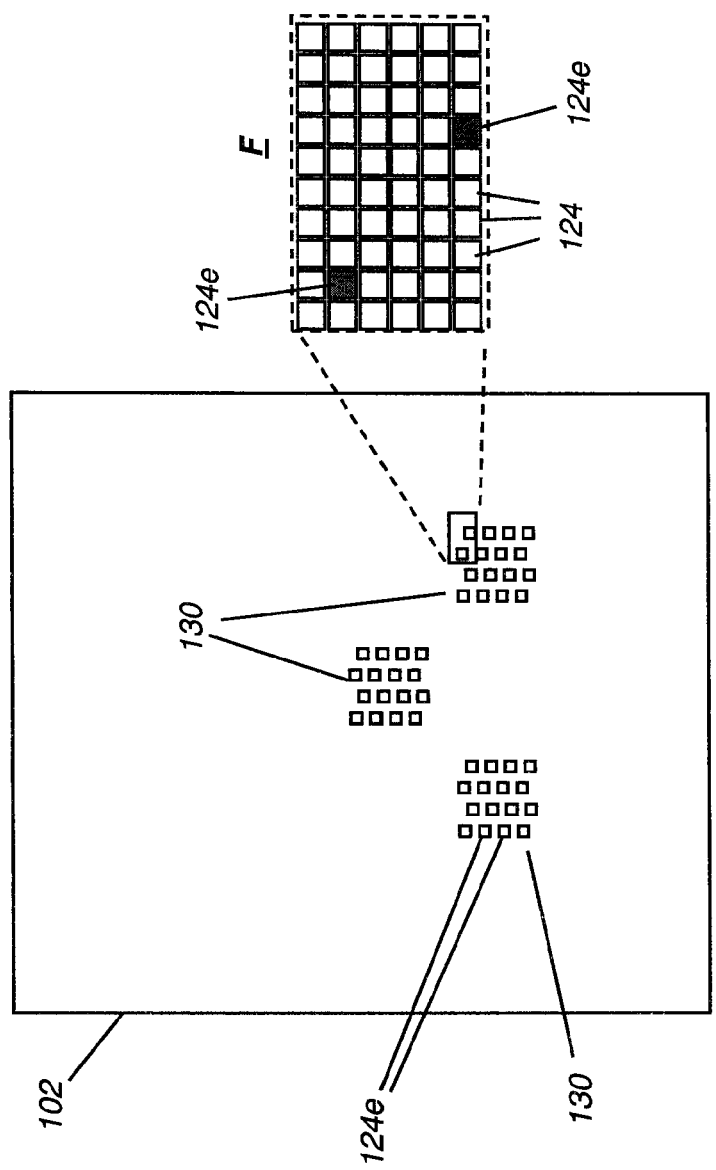
FIG. 12 is a plan view of a digital radiographic imaging detector with an enlarged portion showing placement of pixels used for exposure control sensing.

In one embodiment of the present invention, as shown in FIG. 12, one or more of pixels 124 is used differently as an exposure control sensing element 124e, assigned for the purpose of exposure measurement. A first subset of one or more radiant-energy sensing elements, assigned as exposure control sensing elements 124e, may be contiguous, that is, may be nearest neighbors in the pixel array, or may be distributed over areas of the DR panel 102, separated from each other by one or more pixels 124 that are part of a second imaging subset of radiant-energy sensing elements used for imaging in the standard way, as shown in the example of FIG. 12. Enlarged section F shows one embodiment, with pixels over a portion of DR panel 102, having exposure control sensing elements 124e spaced apart from each other and each of the exposure control sensing elements 124e surrounded by standard imaging pixels 124. Exposure control sensing elements 124*e* can be grouped in patterns to form an exposure sensing region 130 as shown in FIG. 12, or can be more randomly assigned or arranged.

Exposure control sensing elements 124*e* are addressed and operate differently from conventional imaging pixels 124. The conventional imaging pixel 124 is addressed once per exposure, immediately following exposure, for obtaining its stored image signal. The assigned pixel 124*e*, however, can be sampled one or more times during exposure. The signal that is obtained from assigned exposure control sensing element 124*e* is optionally combined with signals from other pixels 124*e* and the resulting value checked, such as by comparison against a predetermined threshold value, for example. The result of this checking process is then used to determine the relative exposure level that has been received by the subject and to terminate exposure when a predetermined targeted exposure level is reached.

Figure 13:
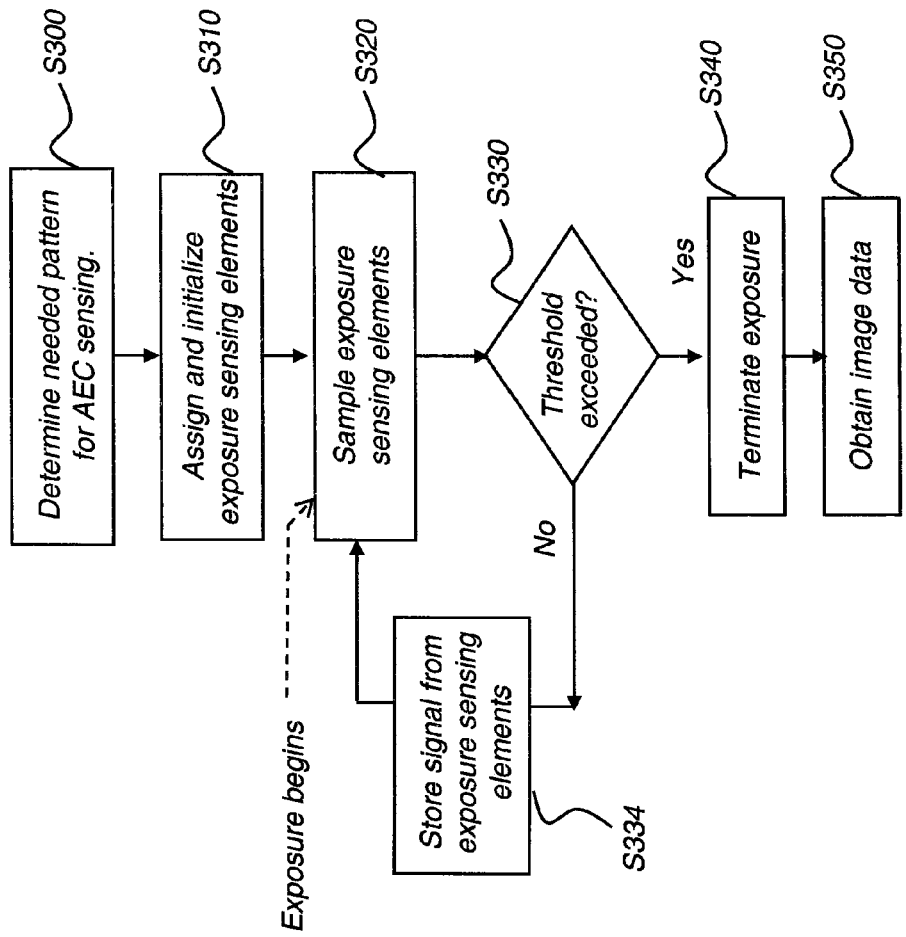
FIG. 13 is a logic flow diagram showing a sequence of steps for exposure control sensing consistent with an embodiment of the present invention.

The logic flow diagram of FIG. 13 shows the sequence of operations for exposure control using an arrangement of exposure control sensing elements 124*e* on DR panel 102 according to one embodiment of the present invention. In an optional pattern determination step S300, the needed pattern for exposure sensing, such as using a fixed or adjustable pattern of exposure sensing regions 130, as shown in FIG. 12 for example, is ascertained. As described previously, there may be a fixed pattern of exposure sensing regions 130 that is always used or serves as a default pattern for a given type of imaging. Alternately, other fixed or variable patterns could be selected for arranging the configuration of exposure control sensing elements 124*e*, including a variable pattern-based on the type of image that is to be obtained or based on placement of the detector relative to the patient. An assignment step S310 is executed when needed, assigning one or more pixels 124 to serve as exposure control sensing elements 124*e* according to the needed pattern.

Embodiments of the present invention allow flexible assignment of radiant energy sensing elements as exposure control sensing elements for each patient exam. Assignment itself can be performed in automated fashion or manually. As was described previously with respect to FIGS. 4A through 5D, there are a number of operator interface utilities available for making this assignment.

The embodiment shown in FIG. 9 provides various tools that can be used for exposure control sensing element assignment. The operator interface on display 64 provides a set of utilities that can be used for manual selection. Camera 30 and the combination of exposure apparatus and detector 12 provide tools for optional automation of selection; both can be used for obtaining types of image data that relate the position of the subject to the digital radiography detector.

According to one embodiment of the present invention, assignment of radiant energy sensing elements is automated by obtaining visible light image data of the patient from camera 30 and using this image to identify the relative location of particular anatomy features, such as the location of neck and shoulders, for example. For lung imaging, for example, the location of the lung fields can be approximated using this data and exposure control sensing elements 124*e* manually or automatically assigned accordingly. Manual assignment, for example, can obtain operator instructions as was described earlier with reference to FIG. 5A. Automatic assignment can utilize known anatomical models that identify the relative placement of internal organs and other structures.

In an alternate embodiment of the present invention, using a pulsed x-ray source, information on anatomy location is obtained from detector 12 as part of, or along with, the image data, by obtaining some amount of radiographic image data following an initial pulse. A subset of the exposure control sensing elements 124*e* can be selected using this partial radiographic image data or other signal information resulting from the first pulse. In addition, iterative sampling can be used to further define the initial selection, such as refining the initial assignment following a second and third exposure pulse, for example, eliminating some of the exposure control sensing elements 124*e* that were initially selected.

Figure 14A:
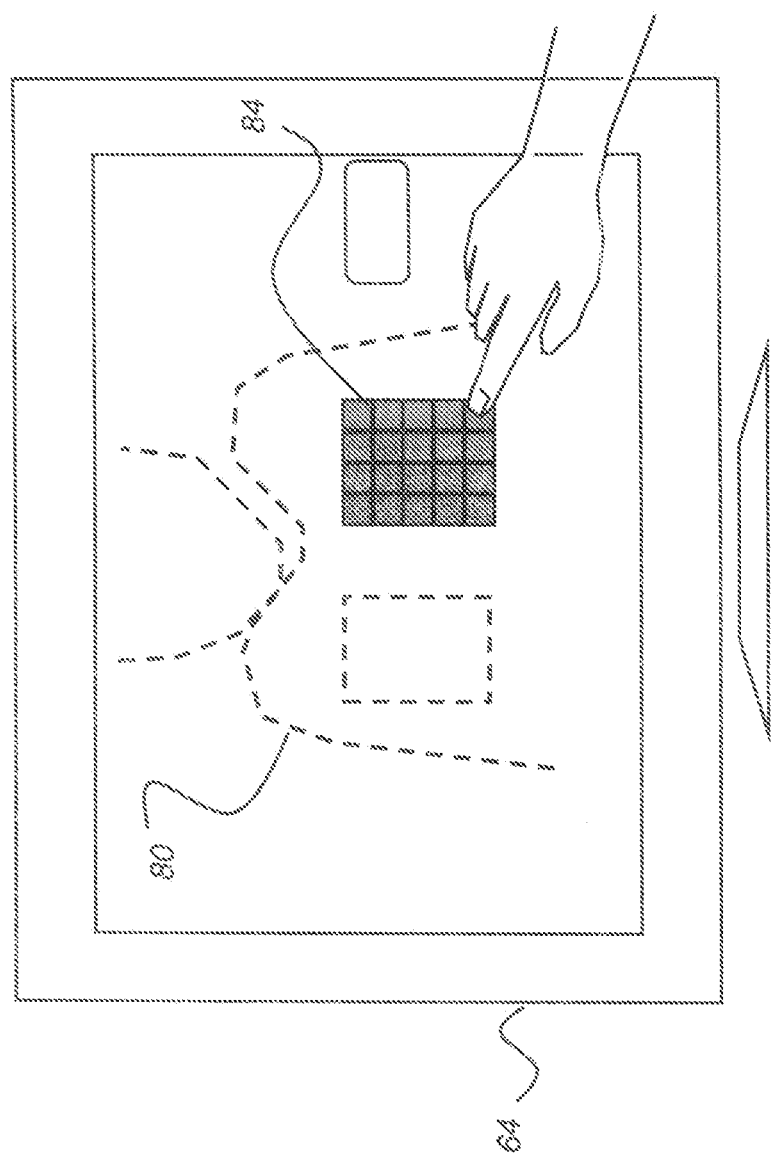
FIG. 14A is a plan view of a display showing a technician selection for an initial sensing area.
Figure 14B:
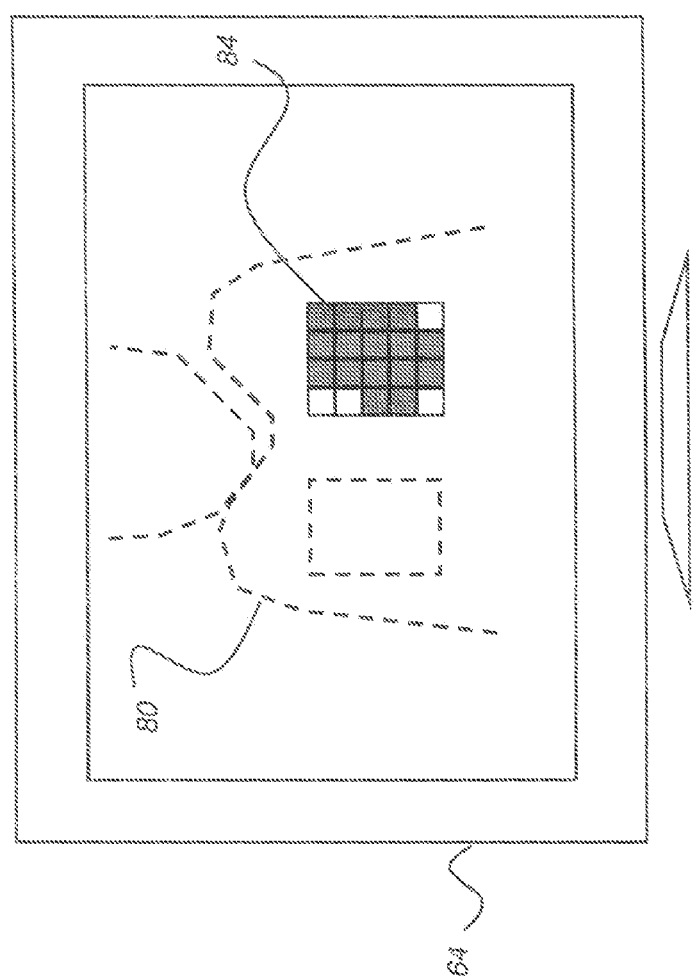
FIG. 14B is a plan view of a display showing a system adjustment to the initial sensing area.

The sequence for exposure control sensing element assignment that is shown in FIGS. 14A and 14B provides an initial manual method and display with an automated refinement based on the sampled exposure measurement. Initially, as shown in FIG. 14A, the technician traces or otherwise provides instructions that indicate an outline on the displayed outline image 80 that coarsely defines a composite radiation measurement region 84, such as the rectangular region shown. Then, as exposure progresses through one or more pulses, sensor control software can measure any of a number of signal conditions that indicate that composite radiation measurement region 84, consisting of one or more exposure control sensing elements 124*e*, should be resized. This can include measurement of statistical data, such as obtaining maximum, mean, median, or mode information on signal strength from any of the groupings of exposure control sensing elements 124*e* selected. As is shown in FIG. 14B, this information can then be used by control logic circuitry to selectively disable measurement from one or more exposure control sensing elements 124*e*, including one or more that were initially selected but eliminated in later processing, thus reshaping the composite radiation measurement region 84, such as by clipping or cropping as shown. This result may or may not be displayed. Rules are applied to restrict the amount of clipping, such as to clip no more than a percentage of the originally defined area or to define default behavior in the event it is not possible to accurately detect a lung field or other area using the measurement data that is obtained. Alternately, control logic can decide to give a higher weighting to one or more exposure control sensing elements 124*e* within composite radiation measurement region 84, based on signal strength or relative location of the sensing element.

In an alternate embodiment, image processing routines are used to determine whether or not there is sufficient contrast or other indication of image quality by successively sampling the assigned exposure control sensing elements 124*e* and assessing their signals as they are known to affect image quality. A repeated check of exposure control sensing elements 124*e* in a region, for example, can be used to determine or approximate the contrast-to-noise ratio in the image data and to terminate exposure when this ratio indicates sufficient contrast. It should be noted that the logic processor for managing assignment of exposure control sensing elements 124*e* and for assessment of signals from those assigned can be on-board the DR detector or on a separate processor, such as on host computer 62 (FIG. 9).

After exposure is initiated, and at predetermined intervals during exposure, one or more of the exposure control sensing elements 124*e* is sampled or polled (that is, addressed) in a sampling step S320. DR detector calibration can also be used to provide gain and offset correction values for exposure control sensing elements 124*e*. During sampling in step S320 (FIG. 13), the data from assigned exposure control sensing elements 124*e* is then adjusted according to the calibration data. This sampling obtains a signal that is indicative of the amount of exposure that has been received. An assessment step S330 follows, in which the signals from one or more exposure control sensing elements 124e are assessed to determine whether or not the targeted level of exposure has been reached or exceeded.

It can be appreciated that assessment step S330 can be executed in any of a number of ways for obtaining an indication of the exposure that has been received. In one embodiment of the present invention, as shown in FIG. 13, signals from multiple exposure control sensing elements 124e are combined, and the combined signal is then compared against a predetermined threshold value for terminating exposure. In an alternate embodiment, individual signals from one or more exposure control sensing elements 124e are obtained and an accumulated score is computed and used to determine when exposure is sufficient and termination is appropriate. If the assessment step S330 indicates that the target exposure has not yet been reached, an optional interim storage step S334 executes, during which the signal or signals obtained from the one or more sampled exposure control sensing elements 124e are stored. This storage further enables use of these pixels for obtaining image data. In this way, exposure control sensing elements 124e can serve both for exposure measurement and for forming an image.

As an example of interim storage step S334, a pixel that has been assigned as an exposure control sensing element 124e is sampled or polled four times during a pulsed exposure sequence. With each sampling, a digital value is obtained, for example: 24, 26, 24, 22. The summed value, 24+26+24+22=96 is compared against a predetermined, stored threshold value 88 in step S330 and used to provide a signal to terminate exposure. Alternately, the summed value thus far is provided with each sampling. The summed value 96 is also used for forming the digital image data for the corresponding pixel in the radiographic image.

Once sufficient exposure has been received, as determined in assessment step S330, the DR detector sends a signal to terminate exposure in an exposure termination step S340. In the system of FIG. 9, this signal goes to host computer 62. In an alternate embodiment, the termination signal goes directly to generator control 68. An image acquisition step S350 follows, in which image data is obtained from DR detector 12.

Embodiments of the present invention can be particularly advantageous when used with exposure apparatus that generate pulsed radiation, enabling one or more selected exposure control sensing elements 124e to be polled following each exposure pulse.

In an alternate embodiment, the signal that is generated at exposure control sensing element 124e is used only for exposure control and no image data is stored for exposure control sensing element 124e. To compensate for the loss of image data at that pixel location, interpolation from surrounding pixel values is then used to calculate an image data value for the corresponding pixel. With reference to enlarged area F in FIG. 12, for example, image data values from neighboring pixels 124 are used to compute the corresponding image data values for the two exposure control sensing elements 124e shown. With this arrangement, exposure control sensing element 124e can have a different size and composition than that of its neighboring imaging pixels 124, such as using a different type of photodiode or other photosensor element, for example.

In another alternate embodiment, exposure control sensing elements 124e are part of DR panel 102 but are not formed in the same way as imaging pixels 124, such as using a different type of photosensor element 122 (FIGS. 10 and 11). Data readout components for exposure control sensing elements 124e also differ from those of standard imaging pixels 124. Calibration techniques that are used for exposure control sensing elements 124e may differ from those used for standard imaging pixels 124.

In an another alternate embodiment, exposure control sensing elements 124e are part of DR panel 102 but are formed on a separate substrate from that used for the DR imaging pixels. The substrate surface that contains these exposure control sensing elements 124e can be disposed so that, with the DR detector in position, this surface lies between the x-ray source and the imaging components or, alternately, is disposed behind the imaging components, which can be substantially transparent to the incident radiation. In yet another alternate embodiment, exposure control sensing elements 124e are discrete elements, not all formed on the same surface but coupled in some way to fixed positions within DR detector 12.

Using pixel locations on the DR panel 102 itself for exposure control eliminates the need for a separate AEC apparatus 40, as was shown in FIGS. 3A, 3B, and 8, while providing AEC capability. This capability also works readily with an operator interface that allows selection, sizing, and positioning of composite radiation measurement regions 52 and 54, such as those shown in FIG. 2D and described previously with reference to FIGS. 5A-5D. An advantage of using the DR detector itself for performing the AEC function relates to positioning information that is readily available. The pixel locations for exposure control sensing elements 124e are each identified and aligned relative to the DR detector, simplifying the task of determining and displaying the position of the AEC sensor elements, as described earlier with reference to FIGS. 7 and 8.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method for sensing a level of ionizing radiation directed from a radiation source through a subject and toward a digital radiography detector, the method executed at least in part by a logic processor and comprising:
   obtaining image data that relates the position of the subject to the digital radiography detector;
   assigning one or more radiant-energy sensing elements of the digital radiography detector as one or more exposure control sensing elements, according to the obtained image data;
   sampling the one or more exposure control sensing elements one or more times during exposure to measure the exposure directed to the subject; and
   providing a signal to terminate exposure according to exposure measurements obtained from the one or more exposure control sensing elements within the digital radiography detector.

2. The method of claim 1 wherein obtaining image data comprises obtaining a visible light image of the subject.

3. The method of claim 1 wherein assigning the one or more radiant-energy sensing elements as one or more exposure control sensing elements comprises accepting instructions entered at an operator interface.

4. The method of claim 1 wherein obtaining image data comprises obtaining radiographic image data from pulsed radiation.

5. The method of claim 1 wherein sampling the one or more exposure control sensing elements further comprises comparing exposure measurements against a threshold value.

6. The method of claim 1 further comprising generating image data using stored exposure measurements for one or more exposure control sensing elements.

7. The method of claim 1 further comprising generating a digital radiographic image from the digital radiography detector following termination of exposure.

8. The method of claim 1 wherein assigning the one or more radiant-energy sensing elements as one or more exposure control sensing elements further comprises associating two or more of the exposure control sensing elements of the digital radiography detector to form a composite radiation measurement region.

9. The method of claim 8 further comprising removing one or more of the exposure control sensing elements from the composite radiation measurement region according to sampled exposure measurements.

10. The method of claim 1 wherein assigning the one or more radiant-energy sensing elements as one or more exposure control sensing elements further comprises distributing the exposure control sensing elements so that two or more of the exposure control sensing elements are spaced apart with radiant-energy sensing elements that serve as imaging pixels between them.

11. A radiographic imaging detector comprising:
a set of radiant-energy sensing elements including a first imaging subset of radiant-energy sensing elements for imaging pixels and a second exposure termination subset of radiant-energy sensing elements to output exposure measurement signals, where different groups of the set of radiant-energy sensing elements of the radiographic imaging detector are selected as the second exposure termination subset of radiant-energy sensing elements according to image content that relates the position of the subject to the radiographic imaging detector, where a first group of the radiant-energy sensing elements is selected as the second exposure termination subset of radiant-energy sensing elements for a first radiographic image and a second group of the radiant-energy sensing elements is selected as the second exposure termination subset of radiant-energy sensing elements for a second radiographic image, where the first group of the radiant-energy sensing elements is different from the second group of the radiant-energy sensing elements.

12. The radiographic imaging detector of claim 11 wherein radiant-energy sensing elements in the second subset provide output signals that are used for imaging, where the second subset of radiant-energy sensing elements are sampled two or more times during the exposure measurement to determine a received exposure amount.

13. The radiographic imaging detector of claim 11 further comprising control logic to output a signal to terminate exposure according to the exposure measurement signals obtained from the second exposure termination subset of radiant-energy sensing elements within the radiographic imaging detector.

14. The radiographic imaging detector of claim 11 further comprising a logic processor to manage assignment of the first group of the radiant-energy sensing elements and the second group of the radiant-energy sensing elements as the second subset of radiant-energy sensing elements.

15. A radiographic imaging apparatus for obtaining a radiographic image of a subject, the imaging apparatus comprising:
a radiation source that is energizable to generate pulsed ionizing radiation;
a radiographic imaging detector disposed in the path of the radiation to form the radiographic image of the subject according to the ionizing radiation received, the radiographic imaging detector having a first subset of radiant-energy sensing elements that provide an image and a second subset of radiant-energy sensing elements that provide one or more output signals that are used for exposure measurement and termination, wherein the first and second subsets are of a variable size and the size is adjustable for the radiographic image, where a first portion of the second subset is selected for a first radiographic image and a second portion of the second subset is selected for a second radiographic image, where the first portion and the second portion are different portions of the second subset; and
a control logic circuit that receives the one or more output signals from the second subset of radiant-energy sensing elements and generates a termination signal according to the received output signals.

16. The apparatus of claim 15 further comprising an operator interface that accepts operator instructions that select elements of the second subset of radiant-energy sensing elements.

17. The apparatus of claim 15 further comprising a projector that is energizable to project an image showing the position of one or more areas of the second subset of radiant-energy sensing elements that provide output signals that are used for exposure measurement.

18. The apparatus of claim 15 further comprising a camera that is coupled to the radiation source and is actuable to provide a visible light image that shows the position of the subject and wherein the second subset of radiant-energy sensing elements is selected according to the visible light image provided by the camera.

19. The apparatus of claim 15, where the second subset of radiant-energy sensing elements are sampled two or more times during the exposure measurement to determine a received exposure amount.

* * * * *